United States Patent
Desai et al.

(10) Patent No.: US 10,695,132 B2
(45) Date of Patent: Jun. 30, 2020

(54) MULTIPLE PROBE ABLATION PLANNING

(71) Applicant: Canon U.S.A. Inc., Melville, NY (US)

(72) Inventors: Devashree S. Desai, Ashland, MA (US); Takahisa Kato, Brookline, MA (US); Lydia G. Olson, Swampscott, MA (US)

(73) Assignee: Canon U.S.A., Inc., Melville, NY (US)

( * ) Notice: Subject to any disclaimer, the term of this patent is extended or adjusted under 35 U.S.C. 154(b) by 98 days.

(21) Appl. No.: 16/027,093

(22) Filed: Jul. 3, 2018

(65) Prior Publication Data

US 2019/0008591 A1 Jan. 10, 2019

Related U.S. Application Data

(60) Provisional application No. 62/530,040, filed on Jul. 7, 2017.

(51) Int. Cl.
*A61B 34/30* (2016.01)
*A61B 34/10* (2016.01)
(Continued)

(52) U.S. Cl.
CPC ............ *A61B 34/10* (2016.02); *A61B 18/02* (2013.01); *A61B 34/20* (2016.02); *A61B 34/25* (2016.02);
(Continued)

(58) Field of Classification Search
CPC combination set(s) only.
See application file for complete search history.

(56) References Cited

U.S. PATENT DOCUMENTS 6,487,431 B1 11/2002 Iwano et al.
9,144,461 B2 9/2015 Kruecker et al.
(Continued)

FOREIGN PATENT DOCUMENTS

WO 2008/139354 A2 11/2008
WO 2014/201108 A1 12/2014

OTHER PUBLICATIONS

Talbot, H., et al., "Interactive Planning of Cryotherapy Using Physically-Based Simulation", Feb. 1, 2014, p. 918200.
(Continued)

*Primary Examiner* — Omar S Ismail
(74) *Attorney, Agent, or Firm* — Canon USA, Inc., IP Division

(57) ABSTRACT

A method of performing a percutaneous multi-probe treatment includes: acquiring a scan image of an object to be treated with multi-probe percutaneous insertions; determining a first point in a region of interest (ROI) in the scan image; determining a second point at a surface of the object in the scan image; generating a reference trajectory by connecting the first point and the second point; arranging, around the first point, a number of third points corresponding to tips of probes to be inserted into the object; generating planned insertion trajectories for the probes based on the number of probes to be inserted and the reference trajectory; and causing a monitor to display superposed on the scan image, at least one of the planned insertion trajectories. The planned insertion trajectories extend in a geometric relationship to the reference trajectory and pass through the third points and through one or more second points.

33 Claims, 14 Drawing Sheets

(51) Int. Cl.
  A61B 34/00     (2016.01)
  A61B 34/20     (2016.01)
  A61B 18/02     (2006.01)
  G06T 7/00      (2017.01)
  A61B 18/00     (2006.01)
  A61B 18/18     (2006.01)
  A61B 18/14     (2006.01)
  A61B 18/20     (2006.01)
  A61B 90/00     (2016.01)

(52) U.S. Cl.
  CPC ............ *A61B 34/30* (2016.02); *G06T 7/0012* (2013.01); *A61B 18/14* (2013.01); *A61B 18/1477* (2013.01); *A61B 18/1815* (2013.01); *A61B 18/20* (2013.01); *A61B 2018/00577* (2013.01); *A61B 2018/0293* (2013.01); *A61B 2018/1425* (2013.01); *A61B 2018/1869* (2013.01); *A61B 2018/2005* (2013.01); *A61B 2034/107* (2016.02); *A61B 2034/252* (2016.02); *A61B 2034/254* (2016.02); *A61B 2034/256* (2016.02); *A61B 2090/374* (2016.02); *A61B 2090/378* (2016.02); *A61B 2090/3762* (2016.02); *G06T 2207/10081* (2013.01); *G06T 2207/10088* (2013.01); *G06T 2207/10132* (2013.01); *G06T 2207/20104* (2013.01)

(56) References Cited

U.S. PATENT DOCUMENTS

| | | |
|---|---|---|
| 2008/0208041 A1 | 8/2008 | Gilboa |
| 2009/0112084 A1* | 4/2009 | Piferi ............... G01R 33/286 600/421 |
| 2009/0171184 A1* | 7/2009 | Jenkins ............... A61B 5/055 600/411 |
| 2009/0259122 A1* | 10/2009 | Larson ............... A61B 5/0555 600/411 |
| 2009/0318804 A1 | 12/2009 | Avital et al. |
| 2010/0063496 A1 | 3/2010 | Trovato et al. |
| 2012/0226145 A1 | 9/2012 | Chang et al. |
| 2012/0237105 A1 | 9/2012 | Mielekamp |
| 2013/0079678 A1* | 3/2013 | Stein ............... A61B 17/025 600/594 |
| 2013/0079790 A1* | 3/2013 | Stein ............... A61F 2/4657 606/102 |
| 2013/0245461 A1* | 9/2013 | Maier-Hein ......... A61B 5/0035 600/476 |
| 2013/0345718 A1* | 12/2013 | Crawford ............... A61B 10/02 606/130 |
| 2014/0128881 A1* | 5/2014 | Tyc ............... A61B 18/0206 606/130 |
| 2014/0171792 A1 | 6/2014 | Dalal et al. |
| 2014/0201669 A1 | 7/2014 | Liu et al. |
| 2016/0008074 A1* | 1/2016 | Glossop ............... A61B 90/11 606/130 |
| 2016/0113632 A1 | 4/2016 | Ribes et al. |
| 2017/0020623 A1* | 1/2017 | Glossop ............... A61B 90/11 |
| 2017/0079720 A1 | 3/2017 | Velusamy et al. |
| 2017/0100195 A1 | 4/2017 | Velusamy |
| 2017/0189127 A1* | 7/2017 | Weir ............... A61B 34/32 |
| 2017/0348061 A1* | 12/2017 | Joshi ............... A61B 17/7089 |
| 2018/0168682 A1* | 6/2018 | Hazard, III ............ A61B 34/30 |
| 2018/0333208 A1* | 11/2018 | Kotian ............... A61B 34/20 |

OTHER PUBLICATIONS

Ren, H., et al, "Treatment Planning of Image Guidance for Radiofrequency Ablations of Large Tumors", IEEE J Biomed Health Inform., May 2014, pp. 920-928, vol. 18, No. 3.

Beyer, L. P., et al, "Stereotactically-navigated percutaneous Irreversible Electroporation (IRE) compared to conventional IRE: a prospective trial", PeerJ 4:e2277; DOI 10.7717/peerj.2277.

Wood, B.J., et al, "Navigation Systems for Ablation", J Vasc Interv Radiol., Aug. 2010, pp. S257-263, vol. 21, No. 8.

Maxio Brochure: Planning and Targeting for CT guided Procedures by Perfint.

Liu, S., et al, "Automatic Multiple-Needle Surgical Planning of Robotic-Assisted Microwave Coagulation in Large Liver Tumor Therapy", PLoS ONE, Mar. 16, 2016, vol. 11, No. 3.

CAScination; CAS-ONE IR, Stereotactic Navigation System for Interventional Radiology Brocure.

* cited by examiner

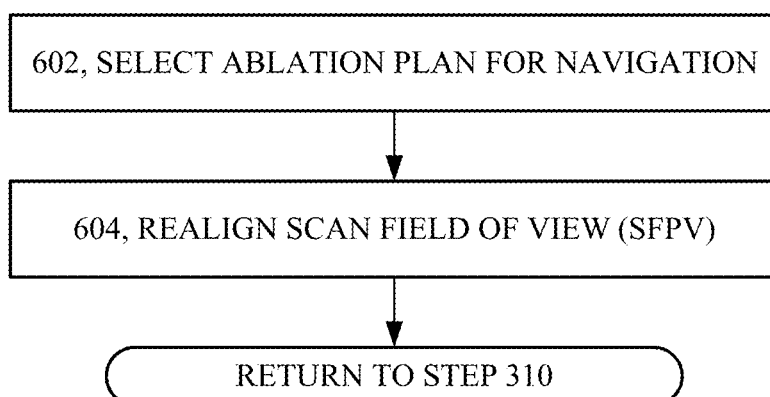
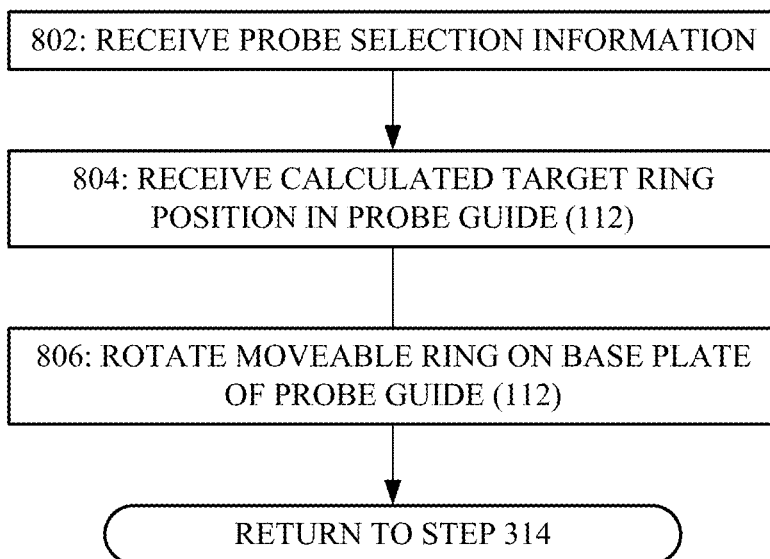

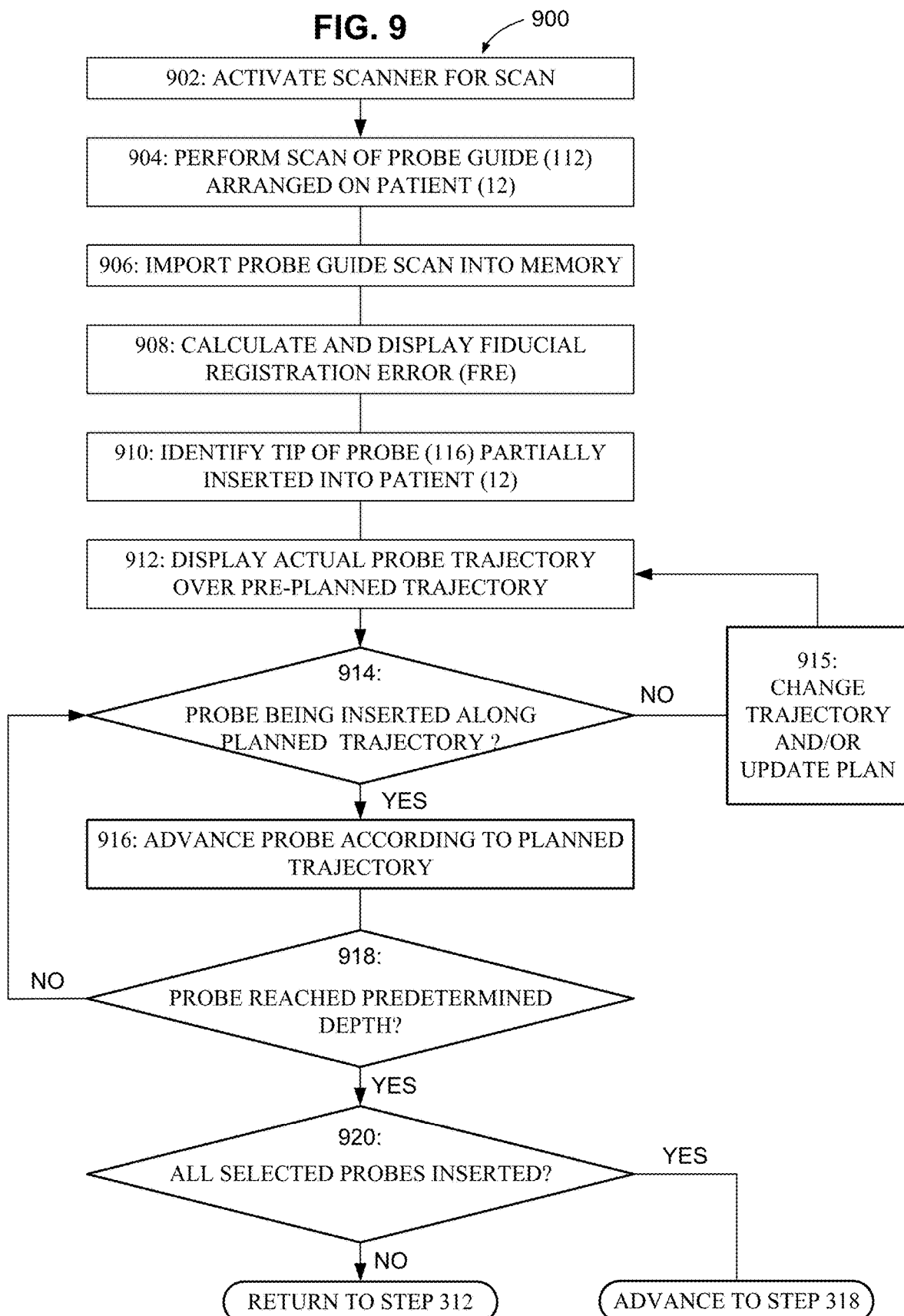

MULTIPLE PROBE ABLATION PLANNING

CROSS-REFERENCE TO RELATED APPLICATIONS

The present application claims priority benefit from U.S. provisional patent application No. 62/530,040 filed Jul. 7, 2017, the disclosure of which is hereby incorporated by reference herein in its entirety.

BACKGROUND

Field of Disclosure

The disclosure of the present application generally relates to image-guided medical interventions, and in particular the disclosed information relates to computer-aided planning, simulation, modeling, and performance of image-guided surgical procedures related to multiple probe percutaneous interventions.

Description of Related Art

Tumor ablation is a surgical procedure involving the destruction of diseased tissue in an animal or human body. For percutaneous ablation, a needle-like hollow probe is inserted into a tumor or lesion to be ablated with the use of ultrasound, computed tomography (CT) or magnetic resonance imaging (MRI) guidance. Solid tumors, such as those found in the liver, prostate, lung, breast, and kidney often are ablated using cryoablation. In cryoablation, a clinician typically passes the needle-like hollow probe into the body through a skin entry point until the tip of the probe reaches a location inside or adjacent to diseased tissue. Then, cooled, thermally-conductive fluid such as liquid nitrogen is pumped through the hollow probe to the target tissue until ice crystals form within the tissue cells and the local tissue freezes into a small volume generally referred to as an "ice ball". With the ice ball surrounding the tumor, ablation occurs in the frozen tissue and the diseased tissue is destroyed. Other ways to surgically destroy diseased tissue include using a probe to introduce electricity (fulguration), heat (radiofrequency or microwave ablation), laser light (laser ablation), radioactive seeds (radiotherapy such as brachytherapy), or chemicals such as absolute alcohol (chemoablation).

In order to destroy large tumors (larger than the volume formed around a single probe tip), the needle-like probe tip needs to be repeatedly repositioned to ablate different parts of the tumor, partly overlapping with one another. This process needs to be repeated several times until the entire tumor is "covered" by the plurality of ablations. Alternatively, multiple probes can be used either simultaneously or sequentially. The use of multiple probes includes using probes having different structure (e.g., different tip size or shape) to cover irregularly shaped tumors (most tumors are not spherically shaped). Therefore, multiple probe ablation involves using two or more different and separate probes. The probes may be used in series to ablate portions of the diseased tissue over time or used in parallel where all probes are inserted before ablation starts and used together to create the ice ball. A clinician may choose multiple probe ablation, for example, in a case where the clinician determines that the shape or size of the diseased tissue is such that one probe is not sufficient to create an ice ball that is large enough to include all the diseased tissue.

In conventional multiple probe ablation, a clinician typically manually plans insertion of a first probe, and manually plans insertion of each next probe. That is, the process is done in an incremental fashion: for the first probe, plan an insertion point, a target point, and a trajectory connecting the insertion point and the target point as a first probe plan, insert the first probe part way according to the plan, scan the first probe in the body, make an adjustment or modification to the first probe plan as needed based on the scan of the inserted probe, finish inserting the first probe, and follow a similar process to insert another probe.

Ablation involves a very complex procedure. However, clinicians predominantly perform the ablation procedure manually and iteratively. Manually planning different trajectories for every probe in a multiple probe ablation procedure increases the time required to perform ablation (i.e., it is inefficient) and may introduce errors (e.g., may affect non-diseased tissue). Also, the more a clinician has to make fine adjustments in each trajectory, the less focus a clinician can devote to creating individual ablations that cooperate to produce a combined ablation zone that is greater than the sum of their separate effects. Further, manually planning discourages clinicians from experimenting with different trajectory options and instead encourages clinicians to make choices that reduce procedure complexity, even though such choices may limit procedure effectiveness. Moreover, the increased time required for manual planning and execution of multi-probe ablation can be detrimental to the patient's comfort and recovery time. Information relevant to proposed improvements on manual planning can be found in, for example, publications US 2016/0113632 and U.S. Pat. No. 9,144,461.

Some known ablation procedures use automatic robotic-assisted navigation to increase accuracy and speed of single or multi-probe image-guided intervention. The proposed robot-assisted procedure can improve the efficiency and safety of large tumor therapy, can reduce the surgeon's workload, and can be helpful for inexperienced medical practitioners. However, robotic-assisted navigation uses cumbersome needle-guide manipulators and actuators, and thus it becomes complicated and expensive due to the size and cost necessary to implement such cumbersome robotic-assisted systems. Information relevant to proposed robotic-assisted needle positioning and navigation systems can be found in, for example, patent publications US 2017/0079720, US 20170100195, and non-patent publication by Liu et al., "Automatic Multiple-Needle Surgical Planning of Robotic-Assisted Microwave Coagulation in Large Liver Tumor Therapy", the public library of science (PLoS) ONE11 (3): e0149482, published: Mar. 16, 2016, https://doi.org/10.1371/journal.pone.0149482".

In percutaneous puncture therapy using a visualization modality and robotic-assisted needle positioning system, it is difficult to reach target tissue because the robotic system itself may interfere with the necessary probe trajectory. For that reason, to reduce the surgery time and burden on the patient, development of a needle placement manipulator for positioning the needle to a target tissue with as few path corrections as possible has been proposed. In particular, a needle placement manipulator that is to be mounted directly on the body surface of a patient has been proposed, for example, by patent application publications US 2014/0275978 and 2018/0103979.

More recently, ablation planning techniques have also been proposed in which the needle placement procedure can be virtually visualized by simulation before the ablation probe is advanced into a target tumor of a patient. See for example, MAXIO™ "Integrated planning, navigation and robotic targeting of tumor ablation", brochure published 2012, and non-patent publication by Beyer et al., "Stereotactically-navigated percutaneous Irreversible Electroporation (IRE) compared to conventional IRE: a prospective trial", (2016), PeerJ, DOI 10.7717/peerj.2277. Some of these known ablation modalities, for example cryoablation, are commonly used with multiple probes to ablate one tumor area. In those modalities, during ablation procedures, the multiple probes need to form a particular configuration, for example a triangular pyramid, around the tumor area to create one large ablation zone by using the multiple probes. Therefore the planning of those ablation procedures with multiple probes becomes more complicated and could be counterproductive without considering the direct correspondence of the probe tip positions to the center of the tumor area. Conventional planning technologies are not known to provide planning support for multi-probe procedures by relating the probe tip positions to the particular configuration that the user defines for the tumor area.

More specifically, an issue that arises in these known image-guided ablation and other percutaneous therapy techniques is that the planned individual trajectories between skin entry point and tumor location often need to be dynamically updated to either avoid vital organs of the patient, to reposition the needle holder and guiding system with respect to the tumor, or to adjust the trajectory due to a change is size and/or location of the tumor (e.g., due to patient movement). Therefore, there is a need for an apparatus and method for planning a synergistic adjustment of the position and/or distance of the tips of multiple probes with respect to the target tumor.

SUMMARY

According to one aspect of the present disclosure, a computer-implemented method for planning a multiple probe percutaneous insertion procedure includes: determining a first point in a tumor region in an image of an object to be examined, determining in the image a second point corresponding to multiple probe insertion at a surface of the object in the image, obtaining number information regarding a number of probes to be inserted into the object, obtaining geometry information of tips of probes associated with the obtained number information, determining, based on the determined first point and the obtained geometry information, third points corresponding to the tips of the probes, generating line segments representing insertion trajectories of the probes, wherein the insertion trajectories pass through the determined third points and intersect the surface of the object at or around the second point, and causing a monitor to display at least a part of the image and the line segments.

The method according to the one aspect further comprises displaying a graphical user interface (GUI) having multiple pictures, wherein each picture corresponds to a number of probes, and each picture illustrates information corresponding to a number of probes. The method according to the one aspect further comprises moving, in response to the ablation server receiving a user input, the displayed third points corresponding to the tips of the probes. The method according to the one aspect further comprises, in response to the ablation server receiving a user input to move one of the third points, moving a remainder of the third points based on a predetermined restriction of distances between at least two of the third points. In the method according to one aspect, the first point is adjacent to a center of a location of the tumor region.

According to another aspect of the present disclosure, a method of performing a percutaneous multi-probe treatment includes: acquiring a scan image of an object to be treated with multi-probe percutaneous insertions; determining a first point in a region of interest (ROI) in the scan image; determining one or more second points at a surface of the object in the scan image; generating a reference trajectory by connecting the first point and one second point; arranging, around the first point, a number of third points corresponding to tips of probes to be inserted into the object; generating line segments representing planned insertion trajectories for the probes based on the number of probes to be inserted and based on the reference trajectory; and causing a monitor to display superposed on the scan image, the reference trajectory, and at least one of the planned insertion trajectories. The planned insertion trajectories extend in a geometric relationship to the reference trajectory and pass through the third points and through one or more second points. In some embodiments, displaying the planned insertion trajectory may comprise displaying an ablation zone that could be formed with the needle(s) inserted with the planned insertion trajectory.

According to a further aspect of the present disclosure, there is provided a multiple probe ablation therapy method. This method includes either the planning probe insertion method as described herein or the method of performing planning as described herein with the additional step of inserting ablation probes along the planned insertion trajectories. An additional step that may be included prior to the planning step is the step of attaching a patient skin-surface mounting device to the skin of a patient at a location near the tumor or other region of interest.

According to yet another aspect of the present disclosure, a method for planning probe insertion in a multiple probe ablation procedure executed by an ablation server, comprises: determining a first point in a tumor region in an image of an object to be examined; determining a second point corresponding to multiple probe insertion at a surface of the object in the image; defining a reference trajectory by connecting the first point with the second point; obtaining number information regarding a number of probes to be inserted into the object; obtaining geometry information of tips of probes of the number, associated with the obtained number information; determining, based on the determined first point and the obtained geometry information, third points corresponding to the tips of the probes; generating line segments representing insertion trajectories of the probes of the number, wherein the insertion trajectories extend along the reference trajectory in a geometric relationship thereof, pass through the determined third points and intersect the surface of the object at or around the second; and causing a monitor to display at least a part of the image and the line segments.

According to one embodiment, the method further comprises: displaying a graphical user interface (GUI) having multiple pictures, wherein each picture corresponds to a number of probes, and each picture illustrates information corresponding to the number of probes, and prompting a user to select the number of probes to be inserted. In some embodiments, the GUI is configured to display the planned insertion trajectory and display an ablation zone formed with the needle(s) inserted with the planned insertion trajectory.

According to one embodiment, the method further comprises: moving, in response to the ablation server receiving a user input, the displayed third points corresponding to the tips of the probe.

According to one embodiment, the method further comprises: moving, in response to the ablation server receiving a user input to move one of the third points, a remainder of the third points based on a predetermined restriction of distances between at least two of the third points.

According to one embodiment, the first point is adjacent to a center of a location of the tumor region; the second point is a center position among plural insertion points on the surface of the object, and the insertion trajectories extend parallel to the reference trajectory, pass through the determined third points and intersect the surface of the object at a distance from the second point.

According to one embodiment, the second point is an insertion point on the surface of the object, and the insertion trajectories extend at an angle with respect to the reference trajectory, pass through the determined third points and intersect the surface of the object substantially at the second point.

According to one embodiment, the method further comprises: generating a reference plane which is perpendicular to the reference trajectory and passes through the second point, and generating a working plane which is parallel to the reference plane and passes through the first point. In this embodiment, the first point is at or adjacent to a center of the tumor region, and the third points are arranged on the working plane substantially equidistant from the first point.

According to one embodiment, the method further comprises, in response to a user input to move one of the third points, moving the remainder of the third points to maintain a predetermined maximum or minimum distance between at least two of the third points. According to this embodiment, the method further comprises, in response to moving the third points, updating the insertion trajectories without updating the reference trajectory, wherein the updated insertion trajectories extend along the reference trajectory pass through the moved third points and intersect the surface of the object at or around the second point.

According to one embodiment, the method further comprises, in response to a user input to move the first point, moving all of the third points such that the third points remain arranged around the first point while maintaining a predetermined distance between at least two of the third points.

According to one embodiment, the method further comprises, generating an image of a probe guide device arranged on the reference plane along the reference trajectory, and displaying on the monitor the image of the probe guide device superposed with one or more insertion trajectories. According to one embodiment, an ablation server stores an ablation application having instructions that, when executed by a processor, cause the ablation server to perform one or more of the foregoing methods.

Further features of the present invention will become apparent from the following description of embodiments with reference to the attached drawings.

BRIEF DESCRIPTION OF THE DRAWINGS

FIG. 6 is a method 600 illustrating a process to place the probe guide 112 on the patient 12 to begin implementing the plan developed in the method 400.

FIG. 8 is a method 800 showing a process for navigating a ring of the probe guide 112 to a target position.

FIG. 9 is a method 900 illustrating a process for updating the pre-operative plan created in step 306 during the insertion of the probe 116 into the patient 12.

DESCRIPTION OF THE EMBODIMENTS

Figure 1:
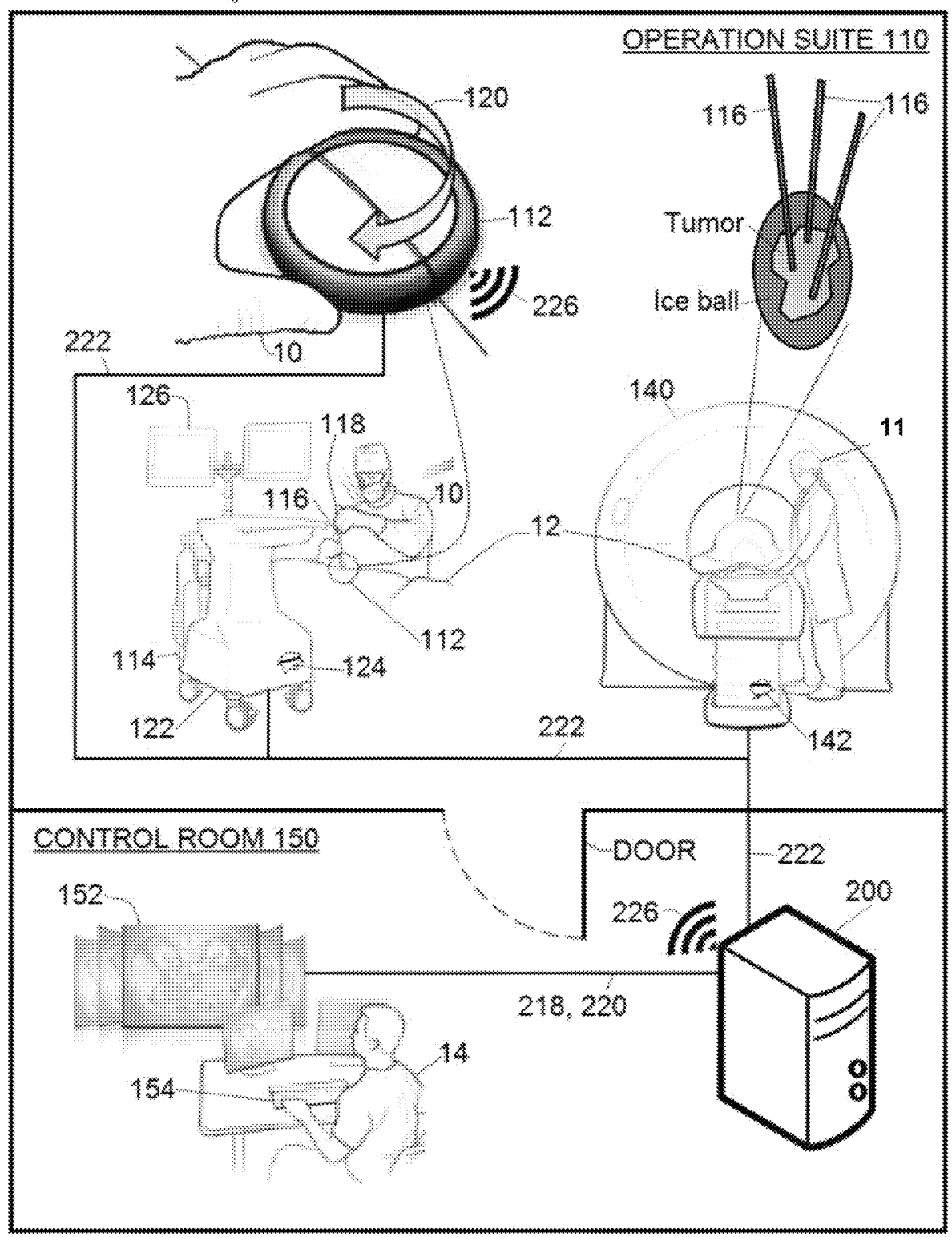
FIG. 1 illustrates a surgical system 100 for performing percutaneous multiple probe treatment of a patient.

Embodiments described below are with reference to the drawings. Throughout the figures, the same reference numerals and characters, unless otherwise stated, are used to denote like features, elements, components or portions of the illustrated embodiments. The present disclosure is not limited to the following embodiments and the following embodiments can be appropriately modified or changed depending on individual constructions and various conditions of apparatuses to which they are applied.

Image-guided percutaneous interventions, such as tumor ablation, require pre-operative planning (planning) and intra-operative surgical execution. Planning includes path planning and tumor coverage optimization. Planning implements patient-specific modeling of probe placement to find a minimal number of trajectories necessary to cover the tumor and a minimal number of ablations along the found trajectories to cover the tumor. To that end, it is also important to plan how to limit then number of probe insertions on the patient, and how to prevent unnecessary damage to healthy tissue or other organs surrounding the tumor.

FIG. 1 illustrates a surgical system 100 for pre-operative planning and intra-operative navigation in multiple probe percutaneous interventions, such as ablation. The surgical system 100 includes an operation suite no and a control room 150, and it may be located in a place where people are given medical or surgical treatment. For example, the surgical system 100 may be located in a hospital or the operation suite no and the control room 150 and their contents may be part of a mobile modular building that can be shipped as cargo around the world and be arranged by themselves as a place where people are given medical or surgical treatment. Indeed, the operation suite no and the control room 150 may be adjacent to each other or may be remote from each other such as in different countries.

The control room 150 may be a room serving as a central space where nonsterile users, such as a control room user 14, can monitor and remotely provide support services to the operation suite no for use by sterile users, such as a clinician 10 and a nurse 11. Personnel (sterile users) serving as a clinician 10 may include an oncologist surgeon who selects the ablation procedure to treat a lesion/tumor, an interventional radiologist (IR) whose expertise is to gather and analyze images to characterize tumors and their size and to review results from a biopsy procedure, a nurse, and an anesthetist. Personnel serving as a control room user 14 may include a CT or MRI technician. The control room 150 includes an ablation server 200 and a control monitor 152 in communication with the ablation server 200.

The operation suite 110 may be a group of one or more operating rooms, equipped to perform surgical operations, and adjunct facilities, such as a sterile storage area, a scrub room, and a patient recovery room. Within the operation suite no, the surgical system 100 may include a probe guide 112, an ablation system 114 (a console), and a scanner 140. During multiple probe ablation, a clinician 10 may use the probe guide 112 and the ablation system 114 to insert one or more probes 116 into a patient 12 using an ablation device 118 and use the scanner 140 to see inside the patient 12 to check on the locations of inserted probes 116. In the case of cryoablation, the inserted probe 116 will cause the formation of an ice ball, or, in case of microwave or radiofrequency ablation, the ablation zone forms a heated volume.

The probe guide 112 may be a wired or wireless, registerable patient-mounted device used by the clinician 10 to help locate a target point of a biological object, such as a lesion or tumor, to help determine the probe target points and trajectories, and to track probe placement when the one or more probes 116 are being inserted through the probe guide 112 into the patient 12. For example, the probe guide 112 may be an image-plane localizer that can be rotated as shown by an arrow 120. The clinician 10 may place the probe guide 112 on the patient and rotate an arc guide on the probe guide 112 at a rotation angle in a way that designates a guide device image-plane within the patient 12. An image inside the patient 12 may be obtained along the guide device image-plane while the probe guide 112 tracks the probes 116 being used through the probe guide 112. The image and information about the rotation angle and the guide device image-plane may be transmitted to an ablation server 200.

The ablation system 114 may be used by the clinician 10 to treat body tissue of the patient 12 and include the ablation device 118, a housing 122, a suite computer 124, and a suite monitor 126. The ablation device 118 may be an instrument used to perform ablation such as cryoablation, chemoablation, fulguration, radiofrequency or microwave ablation, laser ablation, and radiotherapy. In other percutaneous treatments, the ablation device 118 may be replaced by a different instrument, for example, in stereotactic biopsy treatment, the instrument may include multiple biopsy needles. The housing 122 may be an enclosing structure providing support and storage. For example, the housing 122 may physically support the suite computer 124 while the suite computer 124 exchanges communications with the ablation server 200, and may provide space to store ablation fluids and chemicals as well as store ablation devices to produce electricity, heat, and/or laser light. Attached to the suite computer 124 may be input devices such as a keyboard, a mouse, and a microphone, and output devices, such as a speaker and the suite monitor 126. Regarding the suite monitor 126, the suite monitor 126 may be an electronic display device (e.g., LCD screen) to display images, such as an image of ablation plan or an image of a targeted biological object to be ablated.

The scanner 140 includes an imaging modality configured to form pictures of the anatomy and physiological processes of the body of the patient 12. During multiple probe ablation, the clinician 12 may use the scanner 140 to periodically obtain images to track the iterative insertion of the probe 116 along a preplanned trajectory of, for example, four inches (100 millimeters) into the patient 12. To make use of these images, the scanner 140 may include a scanner computer 142 to exchange communications with the ablation server 200. Attached to the scanner computer 142 may be input devices such as a keyboard, a mouse, and a microphone, and output devices, such as a speaker and monitor. The scanner 140 may utilize one or more imaging modalities to perform various medical imaging techniques, such as X-ray computed tomography (CT), digital radiography (DR), endoscopy (ES), magnetic resonance (MR), positron emission tomography (PET), fluoroscopy, and ultrasound (US), or combinations thereof. As illustrated in the upper right corner of FIG. 1, the scanner 140 may be used to obtain an image of multiple probes 116, a tumor, and a treated region surrounding the tumor, where the treated region, is, for example, an ice ball or a thermally heated volume of interest (VOT).

Figure 2:
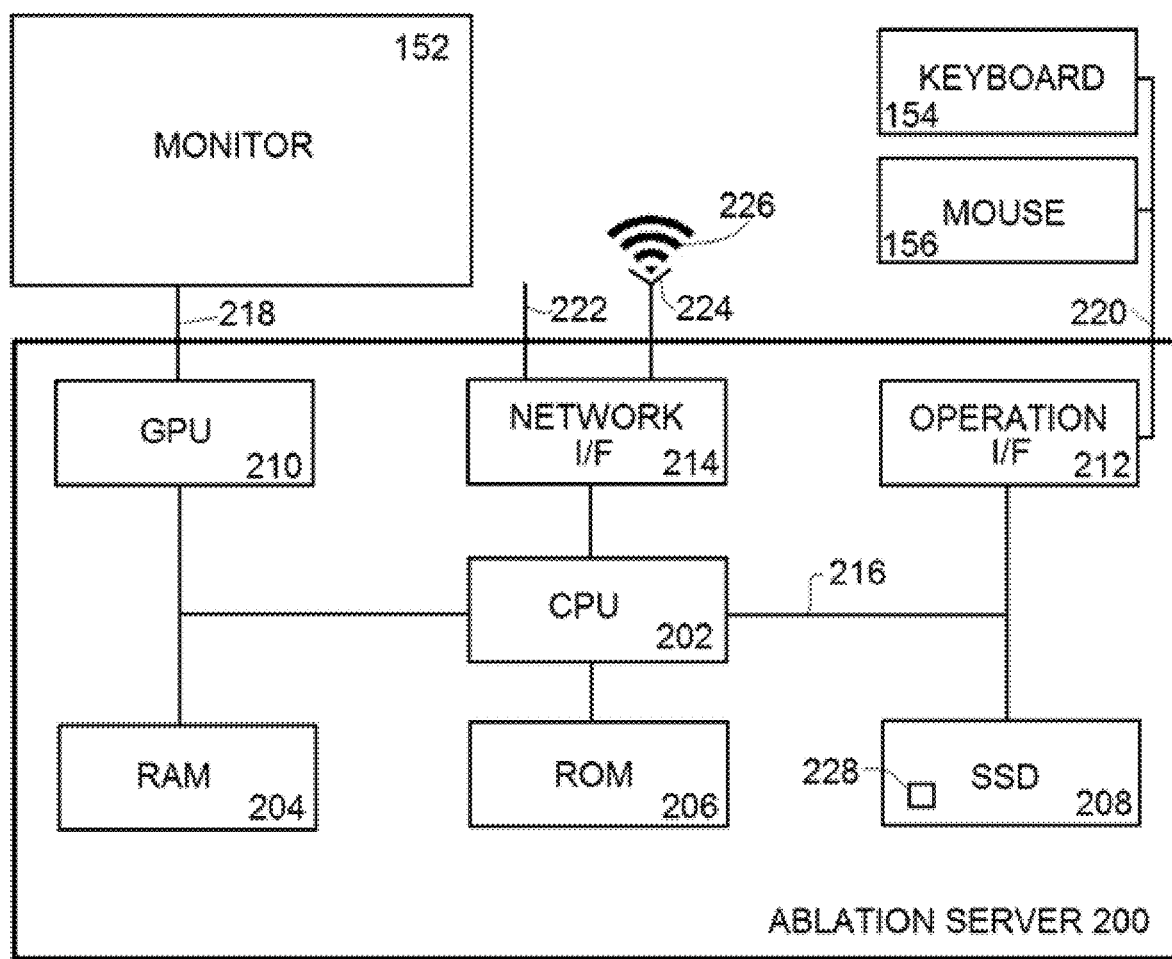
FIG. 2 illustrates hardware of planning server 200 and hardware input and output devices connected to the server 200.

In FIG. 1, the surgical system 100 includes the ablation server 200 in communication with the operation suite no via a wired network 222 or a wireless network 226. However, the ablation server 200 can be located outside of, and remotely from, the operation suite no and the control room 150. The control monitor 152 may be one or more devices used to display images, such as an image of an ablation plan or an image of a targeted biological object to be ablated. The control monitor 152 provides a graphical user interface (GUI) for the control room user 14 to perform pre-operative planning using an ablation application 228 (FIG. 2). In communication with the ablation server 200, the control room 150 may include input devices such as a keyboard 154, a mouse 156 (FIG. 2), and a microphone to discuss procedure with the clinician 10, and other output devices, such as a speaker and the control monitor 152. The control room user 14 may engage with these input and output devices to monitor and remotely support services provided by the clinician 10 in the operation suite 110.

As illustrated in FIG. 1, the ablation server 200 may communicate with the probe guide 112, the ablation system 114, the scanner 140, and the control monitor 152 to assist the clinician 10 and the control room user 14 in planning and performing multiple probe ablation. To store and access images from multiple medical imaging modalities, the ablation server 200 may include, be part of, or be connected to a picture archiving and communication system (PACS).

FIG. 2 illustrates exemplary hardware of the ablation server 200 and exemplary hardware input and output devices connected to the ablation server 200. The ablation server 200 includes a central processing unit (CPU) 202, a random access memory (RAM) 204, a read-only memory (ROM) 206, a memory storage such as a solid state drive (SSD) 208, a graphics processing unit (GPU) 210, an operation interface (I/F) 212, and a network interface (I/F) 214. The solid state drive (SSD) 208 or a similar memory storage device stores therein various programs, images and files, including an ablation application 228. The probe guide 112, the suite computer 124, and the scanner computer 142 may have hardware similar to the ablation server 200.

The CPU 202 contains circuitry to carryout instructions of a computer program, such as the ablation application 228, through processing and control in cooperation with other hardware of the ablation server 200. The RAM 204 is a form of storage that temporarily stores data and machine code of instructions for current use. For example, the CPU 202 may load a computer program onto the RAM 204 and execute the instructions contained in the computer program to perform processes described in this disclosure as well as perform basic input, output, calculation, memory writing, and memory reading processes. The CPU 202 may obtain the computer program from the ROM 206, which is more of long term, non-volatile form of storage, or from the SSD 208, which can store data and the computer program persistently. The SSD 208 can be a memory or storage device different from a solid state drive, such as a hard disk drive, holographic memory disk drive, network-attached or cloud storage, or optical, magnetic tape, or drum based storage. The CPU 202 may be connected with the remaining hardware in the ablation server 200 though a data bus 216.

A surgical operation involving multiple probe ablation is image intense and the graphics processing unit (GPU) 210 may provide specialized electronic circuitry that rapidly interacts with memory to accelerate the creation of images for output to a display device (monitor 152) by efficiently manipulating computer graphics and image processing. The GPU 210 may be connected with the control monitor 152 through a cable 218. In one example, the GPU 210 provides the control monitor 152, in real time, with images related to a multiple probe ablation plan and performance steps and other information about imaging conditions or about a targeted biological object to be imaged and operated on during the procedure. In alternate embodiments, the CPU 202 may be configured to replace and perform the functions of the GPU 210.

As noted above, the ablation server 200 includes interfaces such as the operation interface (I/F) 212 and the network I/F 214. The operation I/F 212 may be connected with the keyboard 154 and the mouse 156 through a cable 220. As such, the operation I/F 212 may assist in communicating information between the keyboard 154 and the mouse 156 and the CPU 202. For example, in a case where the keyboard 154 or the mouse 156 receives input from the control room user 14, a resulting operation signal is input into the operation interface 212 and transmitted to the CPU 202 to instruct the surgical system 100 to set or change imaging, planning and/or performance conditions, and/or to start or end any portion of a method set out in this disclosure. In one example, cables, connectors, communication protocols, and power supply connected with the operation I/F 212 conforms to the Universal Serial Bus standard. As an interface, the network I/F 214 may assist in communicating information such as text data and video between the CPU 202 and devices outside the ablation server 200. A network cable 222 may be connected to the network I/F 214 to transmit and receive wired signals. The network I/F 214 may include a wireless transceiver 224 to transmit and receive a wireless signal 226.

Figure 3:
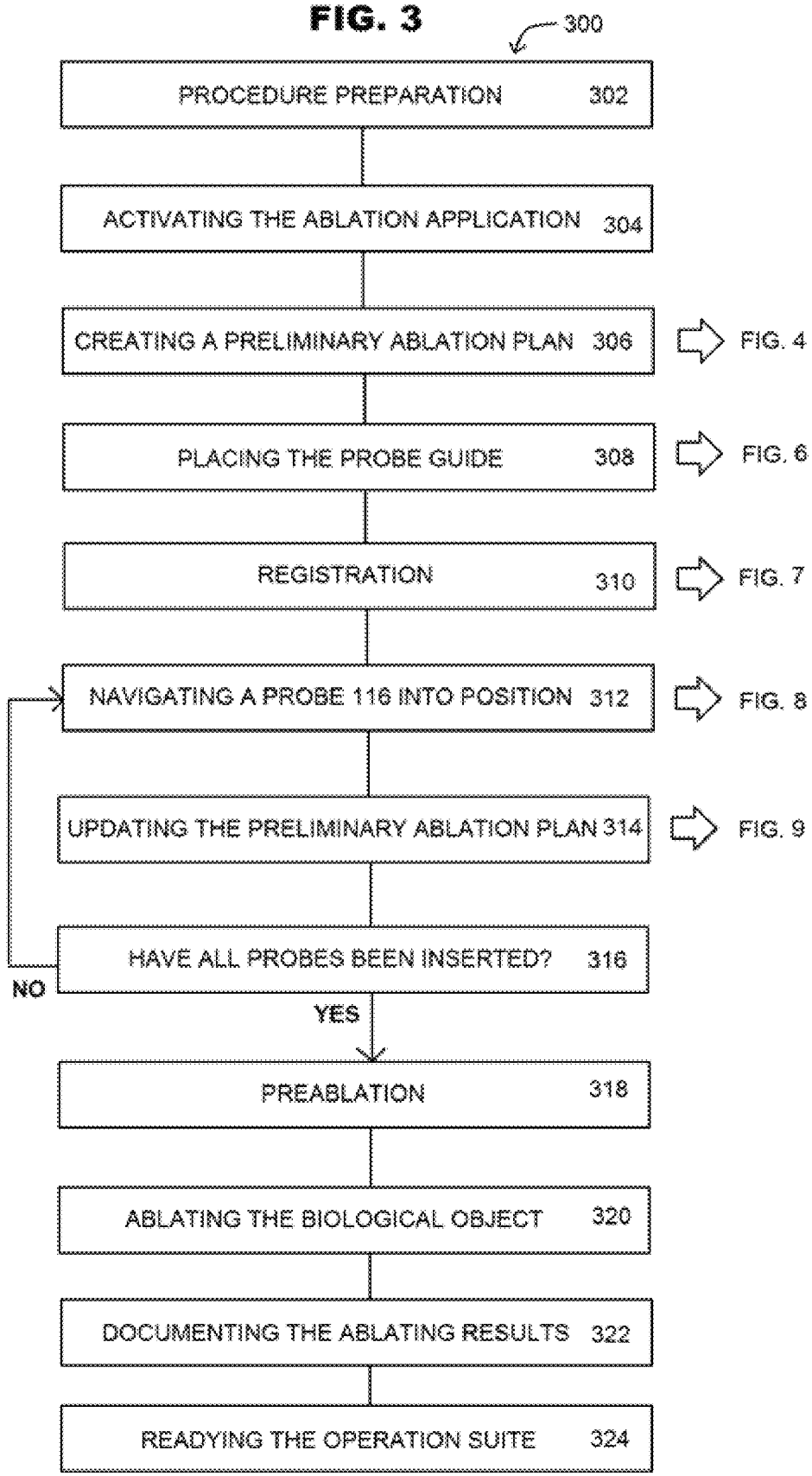
FIG. 3 shows a method 300 providing an overview of performing percutaneous multiple probe treatment of a patient.

FIG. 3 is a method 300 providing an overview of performing a multiple probe ablation procedure. A simplified workflow for an ablation procedure includes at least the following four steps. (1) Setup: This includes connecting all the system components and setting up connections with DICOM to get images from the server and automatically registering the probe guide 112 to the image(s). (2) Planning: This includes planning insertion trajectories according to the desired number of probes, simulating probe insertion, and viewing a model of iceball formation. (3) Probe Insertion: This includes actuating the probe guide 112 to guide one or more probes to the selected target region of interest and performing actual insertion. (4) Monitoring: This includes confirming the actual position of probes inserted with respect to the planned trajectories and saving images of the procedure for reference after the ablation. MRI guided cryoablation procedures are generally performed in an MRI suite or an operating room (OR) with an MRI machine available. For the ablation procedure, except for the probe insertion part, everything else in the workflow happens in the control room generally adjacent to the MRI/OR room. The control room can even include an MRI system workstation where the physician can review and examine the scans.

While the method 300 utilizes a cryoablation procedure using multiple probes as an example, the method 300 may be utilized in other ablation procedures such as thermal ablation procedures, or other percutaneous procedures such as multi-needle image-guided biopsies. To assist in the multiple probe ablation procedure, the ablation server 200 is preprogrammed with specialized planning and navigation software including the ablation application 228 which can be stored in the SSD 208 (or the ROM 206). The ablation application 228 is a type of specialized software having instructions that, when loaded into the RAM 204 and executed by the CPU 202, cause the ablation server 200 to perform operations that assist the clinician 10 (sterile personnel) and the control room user 14 (non-sterile personnel) in computer-aided planning, simulation, modeling, and performance of a surgical operation related to multiple probe ablation. As an application program to perform coordinate functions, tasks, and/or activities, the ablation application 228 may reside within the SSD 208 or parts of the application may reside within multiple servers and work together through CPU 202.

In FIG. 3, at step 302, the method 300 includes procedure preparation. This involves preparing the operation suite no and the patient 12. For example, a nurse 10 may move the ablation system 114, including an anesthesia cart and probes 116 into the operation suite 110 and providing the control room user 14 with a new probe guide package containing the probe guide 112. The nurse 11 may bring the patient 12 into the operation suite 110 and position the patient on the bed for the scanner 140. An anesthesiologist may anesthetize the patient 12 to allow painless performance of the medical procedure and reduced patient movement. The nurse 11 then may create a sterile area in and around an intended skin entry points for the needle-like probes 116 and may adhere a disposable skin marking grid on the sterile area. The skin marking grid helps correlate physical dimensions to what to see in an image scanned by the scanner 140. From step 302, the method 300 proceeds to step 304.

At step 304, the method 300 includes activating the needle guidance system and launching the ablation application 228. This may include the control room user 14 powering up the server 200, launching the ablation application 228 and logging into the ablation application 228 via a graphical user interface (GUI). Once logged in, the control room user 14 may start a new case by receiving information about the patient 12 from a remote device, e.g., a hospital information system (HIS), a radiology information system (RIS) or a picture archiving and communication system (PACS). Patient information may include information, such as name and medical record number (MRN), entered into the new case. Step 304 may also include scanning a barcode of the still-sealed new probe guide package containing the probe guide 112 into the ablation application 228. The ablation application 228 then may use the received serial number and firmware version of the probe guide 112 to search a local database or a remote database over the internet, for example, to confirm the validity of the probe guide 112. Once its validity is confirmed, the nurse 11 may remove the sterile probe guide 112, place it on a sterile table and turn it on to establish communications between the probe guide 112 in the operation suite 110 and the ablation server 200 in the control room 150.

With the anesthetized patient positioned in the scanner 140, the ablation application 228 causes the scanner 140 to conduct a scout scan of the area containing the disposable skin marking grid. In computed tomography (CT) a scout scan is a mode of operating the CT system. A scout scan is a preliminary image obtained prior to performing the actual major portion of a CT study. The scout scan is a reference image generally used to prescribe axial CT slices and to display slice locations rather than for direct diagnosis. There may be several reasons to obtain a scout scan, e.g., to make sure the region of interest is included in the field of view, to check the exposure technique, or to obtain a baseline prior to administration of contrast material. In the process of step 302, the scout scan serves to make sure the region of interest is included in the field of view.

From step 304, the method 300 proceeds, in chronological order, from step 306, through steps 308, 310, 312, and 314. Step 306 includes creating a preliminary ablation plan (pre-operative plan) to determine where to put the probes 116 and is discussed in detail in connection with a method 400 of FIG. 4. Step 308 includes placing the probe guide 112 on a surface (skin) of the patient 12 and is discussed in detail in connection with a method 600 of FIG. 6. Step 310 includes registration of fiducials and is discussed in detail in connection with a method 700 of FIG. 7. Step 312 includes positioning of the probe guide 112 to a target position and partially inserting the probe 116 into the patient 12 and is discussed in detail in connection with a method 800 of FIG. 8. Step 314 includes updating the preliminary ablation plan created in step 306 to iteratively finalize the insertion of the probe 116 and is discussed in detail in connection with a method 900 of FIG. 9. The method 300 proceeds from step 314 to step 316.

At step 316, the method 300 determines whether all probes have been inserted into the patient 12. If all probes have not been inserted into the patient 12 (NO at step 316), the method 300 returns to step 312. If all probes have been inserted into the patient 12 (YES at step 316), the method 300 proceeds to step 318.

At step 318, the method 300 includes a pre-ablation procedure. The control room user 14 engages the ablation application 228 to cause the scanner 140 to obtain a scan of the patient 12 using the scanner 140 and imports the scan into the ablation application 228. After the control room user 14 moves through features of the ablation application 228, the ablation application 228 automatically activates the wireless transceiver 224 to transmit and receive a wireless signal 226 (FIG. 2).

At step 320, the method 300 includes ablating the biological object (e.g., target tissue or tumor). When all probes have been inserted into the patient 12 and a current scan obtained, the ablation application 228 causes, in the case of cryoablation, the liquid nitrogen to be pumped through the hollow probe 116 to the biological object (target tissue). During this process, the ablation application 228 causes the scanner 140 to periodically scan the formation of the ice ball until the ablation process is completed. From step 320, the method 300 proceeds to step 322. Similarly, at this step, in case of thermal ablation, an energy source such as microwave or thermal energy is directed to the probe 116 (in this case, there is no need for the probe to be hollow) to the biological object (target tissue). During this process, the ablation application 228 causes the scanner 140 to periodically scan the formation of the thermally heated region until the ablation process is completed.

At step 322, the method 300 includes documenting results from ablating the biological object (e.g., tumor). The ablation application 228 causes the scanner 140 to scan the ice ball and import the resulting image into the ablation application 228 as a post ablation key scan. Based on input from the control room user 14, the ablation application 228 creates an overlay of a pre ablation scan with the post ablation key scan to allow the clinician 10 to assess whether the procedure was successful. The ablation application 228 receives input notes to the key scan as part of a report and exports the report to the picture archiving and communication system (PACS). The control room user 14 then logs out from the ablation application 228. From step 322, the method 300 proceeds to step 324.

As step 324, the method 300 includes readying the operation suite no for a next medical procedure. After ablation completes (e.g., after a preset time), probe 116 are removed, and clean-up is performed, including, for example, applying a bandage to the patient at the insertion point if no more probe insertion is needed. Waste from the procedure is disposed of, sterile drapes are removed, anesthesia is stopped, the patient 12 is rolled out of the operation suite no, the operation suite no is cleaned, and the ablation system 114 is unplugged and moved to storage. Method 300 ends once the operation suite no is ready for a next medical procedure.

Figure 4:
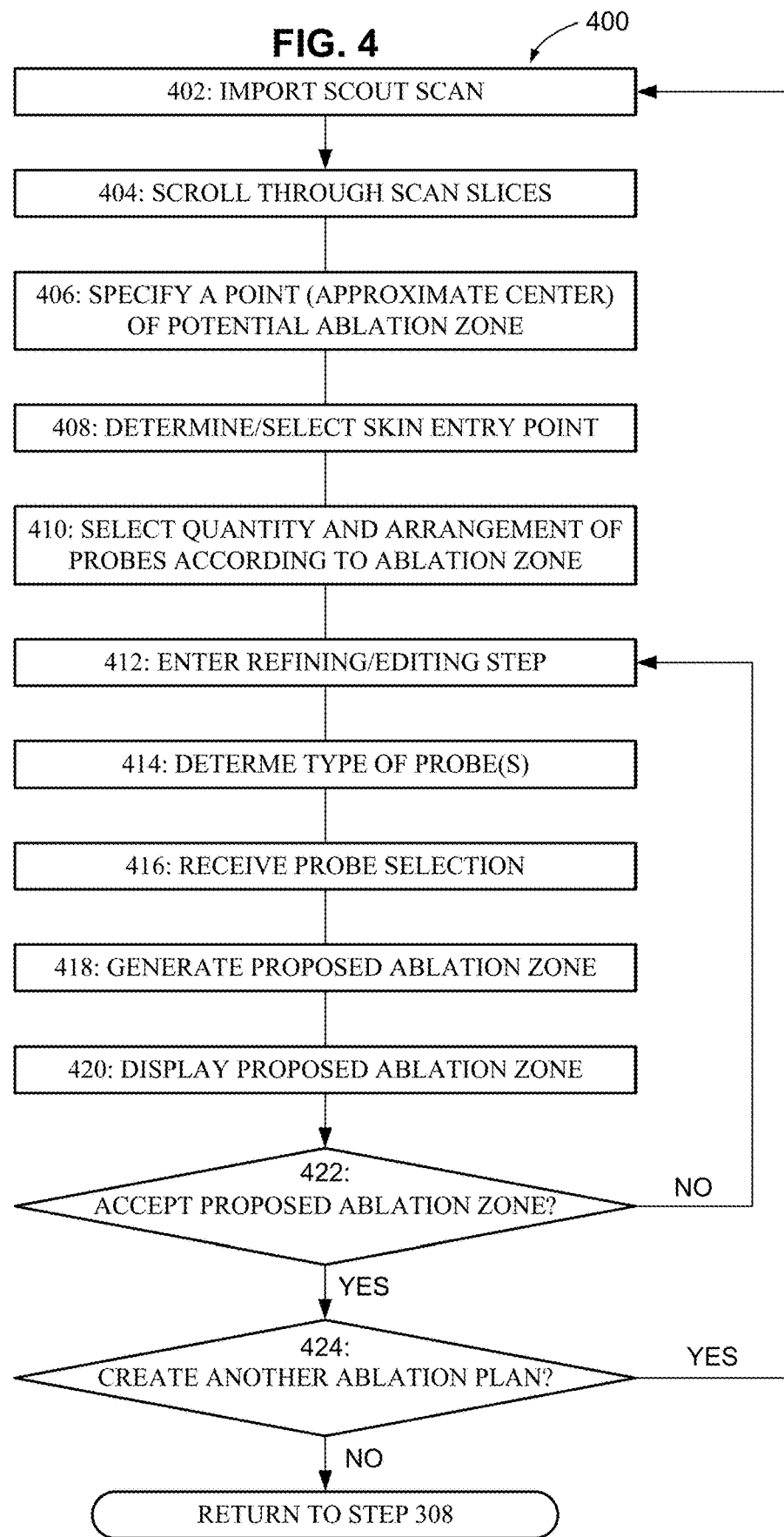
FIG. 4 is a method 400 for creating a pre-operative plan for percutaneous multiple probe treatment.

FIG. 4 is a method 400 showing a process to create a preliminary ablation plan for multiple probe ablation (an example of multi-probe percutaneous procedure). A preliminary ablation plan (pre-operative planning) includes specifying a center of ablation, a skin entry point, and defining one trajectory vector (or reference trajectory) by connecting the center of ablation to one skin entry point. Based on the one trajectory vector, an insertion trajectory for each of one or more probes 116 is planned using the trajectory vector as a reference trajectory.

Recall that, at the end of step 304, the ablation application 228 caused the scanner 140 to conduct a scout scan of the area containing the disposable skin marking grid. The scout scan may be used to plan and obtain scan slices. At step 402 in method 400, the ablation application 228 imports this scout scan into the SSD 208 of the ablation server 200.

At step 404, the clinician 10 scrolls through scan slices to visually locate a biological object such as a tumor or lesion for ablation as well as an approximate center of a potential ablation zone/area for that biological object.

At step 406, the ablation application 228 receives an input from the clinician 10 specifying the potential ablation zone or an approximate center thereof. That is, the clinician 10 (user) can manually specify an area in the scan slice image as the potential ablation zone, and the ablation application 228 can be configured to automatically estimate an approximate center of the potential ablation zone. Alternatively, the user can visually identify the potential ablation zone and then manually identify an approximate center of the potential ablation zone. Further alternatively, the ablation application 228 can include a sub-routine program configured to automatically estimate an approximate center of the potential ablation zone by automatically analyzing image characteristics (e.g., contrast patterns) of one or more the scan slices and determining if a current scan slice has at least one pixel with a certain level of contrast. Regardless of the manner in which the potential ablation zone is specified, at least one pixel can be specified to serve as a first point in a tumor region in an image of an object (e.g., the patient 12) to be examined. In one example, the first point may be adjacent to or at the center of a volume of interest like a tumor region. Since, as disclosed herein, the location of the first point can be manually adjusted during the pre-planning process, it is not strictly necessary for the user to specify an exact center of the potential ablation zone. As long as the user can specify at least one or a few pixels (or voxels) within the scan slice as part of the potential ablation zone, the planning software of ablation application 228 can register the user's selection as the specified first point.

The clinician 10 then takes steps to select one skin entry point. To do this, the clinician 10 may scroll through the scan slices until the disposable skin marking grid is found and select the one skin entry point based on the disposable skin marking grid. Alternatively, the scan entry point can be selected from scrolling around the edge of the object shown in the scout scan and estimating a position of the probe guide 112. Specifically, it is difficult to change the insertion point after the actual probe guide is mounted (taped) onto the patient. Therefore, is advantageous during pre-planning to ensure that the tumor is well inside the area accessible from the probe guide 112. If it is not, then the physician needs to take of the robot which has been taped down to the patient and again clean the new area and tape the robot down. To avoid this time consuming process, the interface would provide a quick way of determining the right insertion point. To do this, a fiducial bead would be placed in the approximate area of the insertion point before taking the scout scan. This scan would then be used to try insertion points along with the cone of approachable area. The physician could drag the fiducial (and cone attached) along the outer edge of the axial scan to determine the most appropriate insertion point that would cover the already specified potential ablation zone. Here, the physician can use the actual fiducial placement as a reference point and then incrementally edit the insertion point as needed to ensure appropriate coverage of the potential ablation zone.

At step 408, the ablation application 228 receives an input indicating the one skin entry point selected by the clinician 10. This one skin entry point will serve as a second point at a surface of the object (e.g., the patient 12) in the image. On receiving the input indicating the one skin entry point, the ablation application 228 automatically creates a reference trajectory at step 408 by connecting the selected point (center) of ablation zone and the one skin entry point.

Figure 10A:
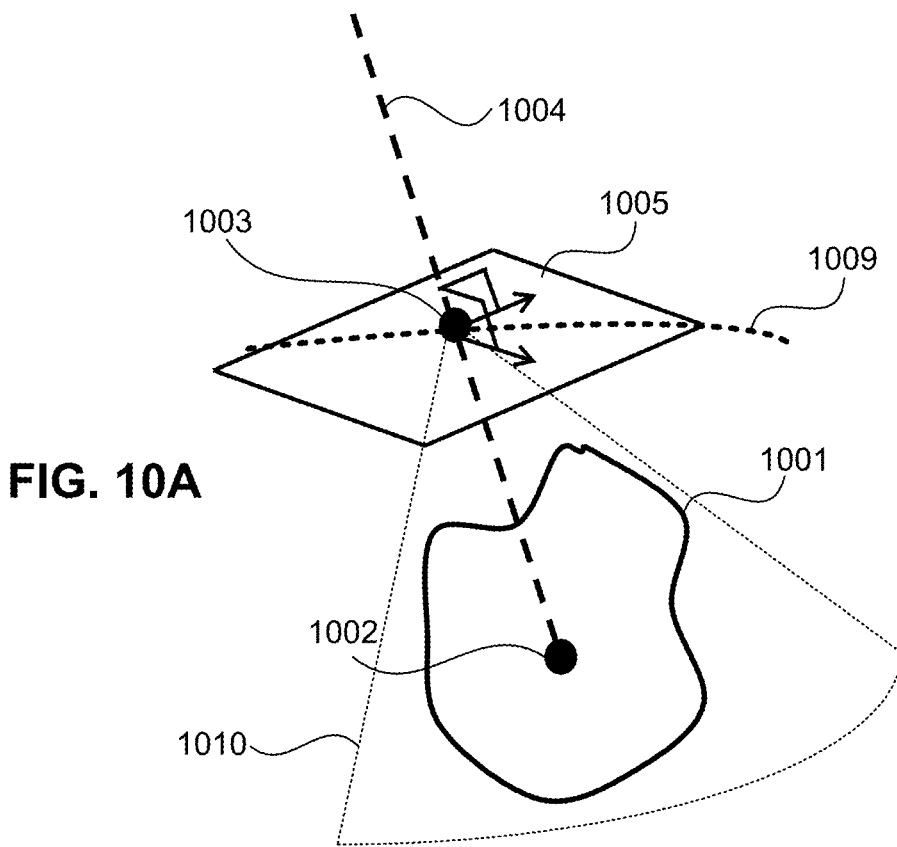
FIG. 10A illustrates an example of the processes carried out in steps 406 and 408.

FIG. 10A illustrates an example of the processes carried out in steps 406 and 408. At step 406, the user defines a point of interest in a tumor region 1001 of a scan slice. In this embodiment, the point of interest is the approximate center of a potential ablation zone that the user defines as a first point 1002. At step 408, the user also defines a second point 1003 in the scan slice. The second point 1003 is a skin entry point which is selected based on the disposable skin marking grid being observed in the scan slice. In the case where a disposable skin marking grid is not used when obtaining the scan slice, the user may select the second point 1003 as an approximate location, e.g., the closest point between the first point 1002 and the skin 1009 of the patient 12. Alternatively, as explained above, would advantageous to select the skin entry point based on an estimated position of the probe guide 112 to be used during the actual procedure. To that end, the second point 1003 (skin entry point) can be selected based on a fiducial marker being observed in the scan slice and based on an area of coverage 1010 (a cone of coverage) accessible from the probe guide 112.

After defining the first point 1002 and second point 1003, the planning software of ablation application 208 generates a trajectory vector (reference trajectory 1004) by connecting the first and the second points 1002 and 1003. At the same time, the planning software of ablation application 228 also generates a reference plane 1005. The reference plane 1005 is perpendicular to the reference trajectory 1004 and passes through the second point 1003 tangentially to the patient's skin 1009. As stated above, the reference trajectory 1004 is the line between a designated skin entry point to the approximate center of the tumor area; thus, the reference trajectory can be defined in the same scan plane of a single scan or among multiple scans. In this regard, the reference trajectory 1004 could be considered similar to defining a single needle trajectory. However, in accordance with the present disclosure, the reference trajectory 1004 does not define a needle trajectory, but it defines a "reference" to the multiple needle trajectory based on the configuration (geometry and number of probes) to be chosen by the user. Therefore, in the planning of multi-probe insertion, the reference trajectory 1004 is not the same as a needle trajectory. The planned insertion trajectory (needle trajectory) will have a geometric relationship to the reference trajectory. For example, for three needles in a triangular pattern, the reference trajectory would be the geometric center of the triangular pyramid formed by the inserted needles (See FIG. 12A). Similarly, for four needles in a square pattern, the reference trajectory would be the geometric center of the square pyramid formed by the inserted needles. In other examples, where the needle trajectories are parallel, the reference trajectory is the geometric center of, for example, of the triangular cylinder (for three needles in a triangular pattern). Similarly for a circular arrangement of needles/probes, the reference trajectory would serve as the geometrical axis of cylinder formed by the arrangement of the probes. This geometrical relationship of the reference trajectory to the planned insertion trajectories enables the user to more intuitively determine whether a planned trajectory is appropriate or not.

The reference trajectory 1004 and reference plane 1005 are representative features of an arrangement (geometry) of the multiple probes in the next step. In this embodiment, the reference trajectory 1004 will become a centroid of the arrangement of the multiple probes at the beginning of the planning. In the same manner, the reference plane 1005 will become the plane (reference plane) to include all representative points of the multiple probes at the beginning of the planning. The user can define the reference trajectory 1004 by selecting the first point 1002 and second point 1003. The first point 1002 is related to the tumor area. The clinician can select this first point 1002 by the intention of treatment. Generally, the tumor center is one of the primal representative points for the first point 1002. On the other hand, the second point 1003 is related to the insertion point. This embodiment assumes that the second point 1003 is the skin entry point of the multiple probes in the case that the multiple probes are to share the same skin entry point (see FIG. 12A). In other embodiments, when more than one skin entry point is used, the second point 1003 could be the center position among the skin entry points of the multiple probes (see FIG. 12B). Therefore, the second point 1003 (and any of the first and third points) is not necessarily a "point" in the mathematical sense; rather the second point 1003 is a place to indicate an approximate position through which a probe 116 would advance towards a designated target. Since a physical probe has a definite dimension, the point may have a diameter of, say, 0.2 mm to 2.0 mm or more. Accordingly, in the specification and claims, a probe passing "substantially" through or located "substantially" at a point allows for a measure of tolerance based on the size of the actual probe being used. In this regard, at step 408, the planning software of the ablation application 228 determines a selected skin entry point in response to detecting a user section of at least of few pixels in the slice scan and accordingly adjusts the size of the entry point based on the actual size of the probe 116.

At step 410, the ablation application 228 prompts the control room user 14 to select a probe arrangement having a desired number of probes 118 to be used for the ablation procedure. Here, the ablation application 228 may obtain number information regarding a number of probes 116 to be inserted into the object (e.g., the patient 12). In the same or a separate step, the geometry information for the probe tips 116 may be obtained. Thus, the ablation application 228 may obtain this geometry information correlated to the obtained number information. The geometry information may be defined manually by the clinician 10, may be pre-defined based on the number of probes 116 to be inserted, or may be some combination thereof (e.g., several different geometries for multiple probes may displayed to the clinician for selection, with a default for instances where the clinician does not choose to select the geometry.

Figure 10B:
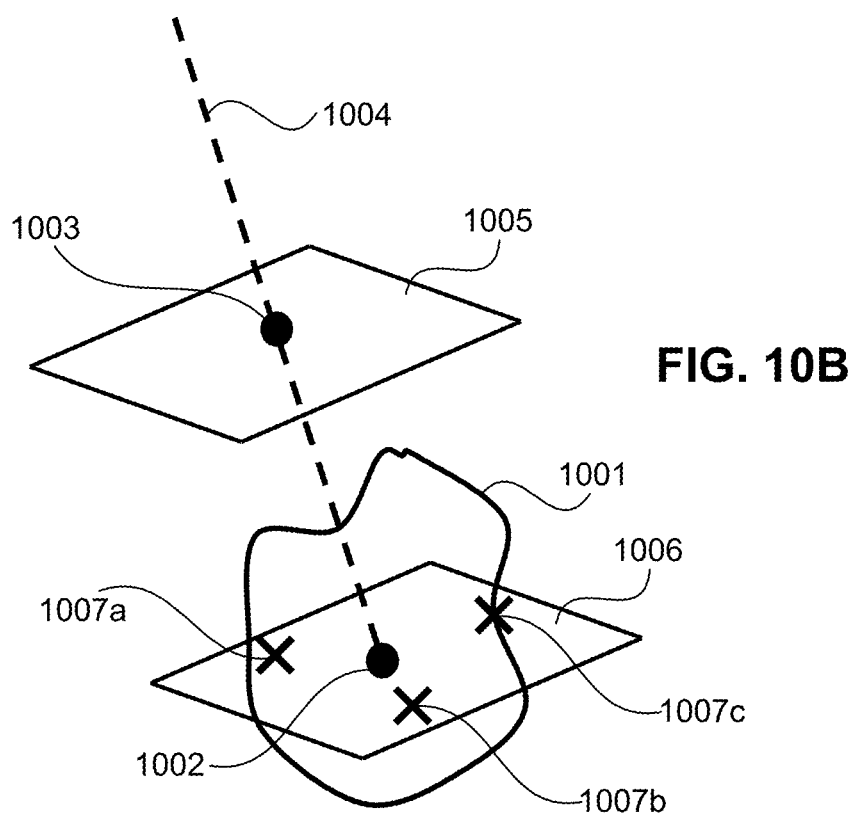
FIG. 10B illustrates an example of processes carried out at steps 410 and 412.

FIG. 10B illustrates an example of processes carried out at steps 410 and 412. At step 410, the user determines the quantity (number) and arrangement (geometry) of probes necessary to cover the volume of interest (tumor). After that, the planning software of ablation application 228 causes the CPU 202 to display (e.g., in monitor 152) a plurality of third points 1007a, 1007b, 1007c with a predetermined arrangement. The third points 1007a, 1007b, 1007c define representative target points for each of the multiple probes 116 according to the quantity of the probes that user has determined to be necessary. For example, each of the representative points (third points 1007a, 1007b, 1007c) can be the target for a tip of each of the probes 116, or each of third points 1007a, 1007b, 1007c can represent the center of the ablation zone of each probe. To facilitate visualization and arrangement, the third points 1007a, 1007b, and 1007c can be initially arranged by the planning software on a working plane 1006. The working plane 1006 is a plane parallel to the reference plane 1005. Specifically, upon receiving the number and geometry of probes, the planning software of ablation application 228 defines the working plane 1006 as a plane perpendicular to reference trajectory 1004 passing through the first point 1002. Then, the ablation application 228 arranges the third points 1007a, 1007b, 1007c on the working plane 1006 approximately equidistantly from first point 1002. By having the third points 1007a, 1007b, and 107c arranged on the working plane 1006 as the initial (default) positions, the user can easily confirm, at a glance, the position of each of the third points 1007a, 1007b, and 1007c with respect to the first point 1002 and with respect to the reference trajectory 1004.

Figure 5:
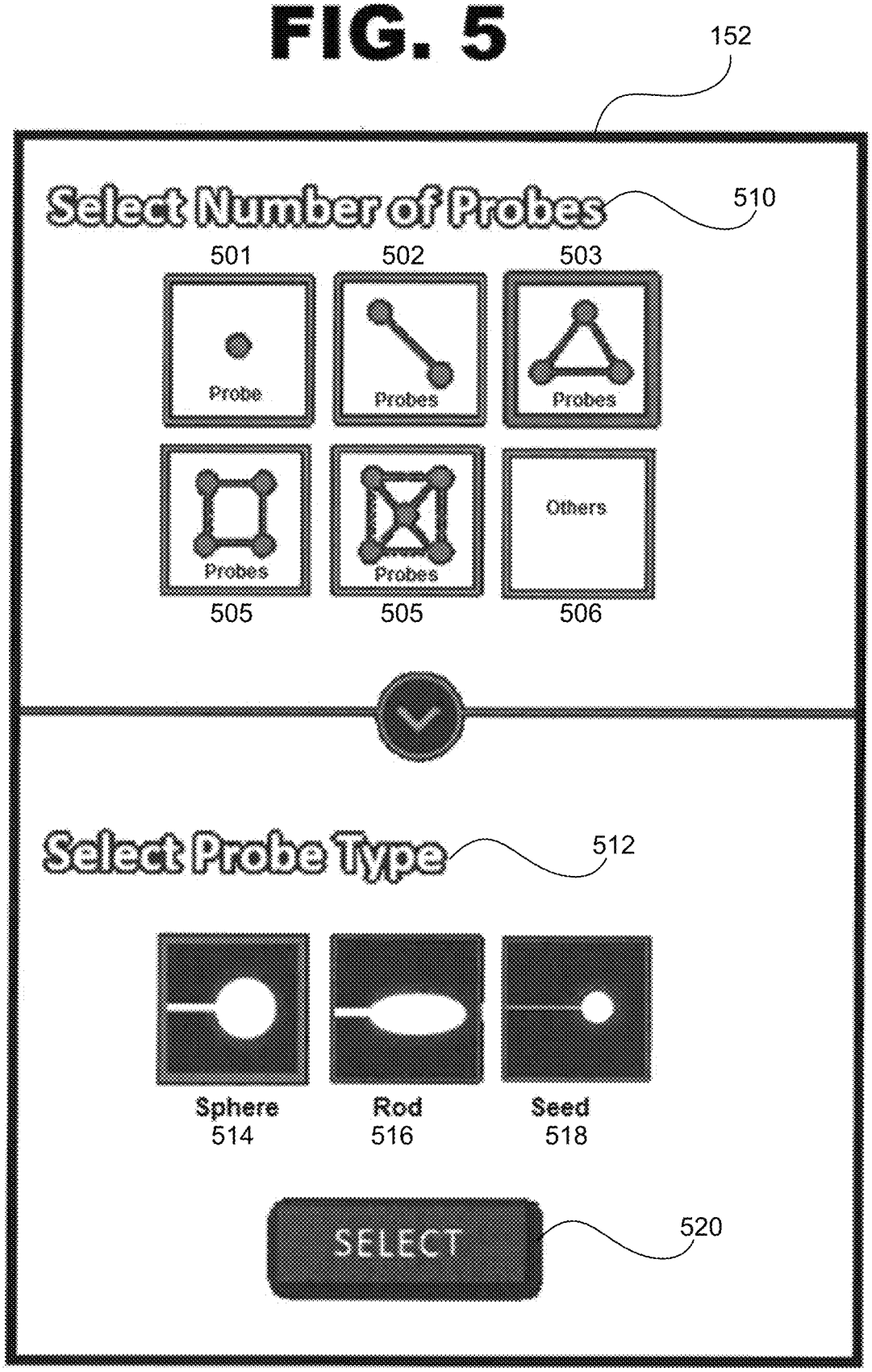
FIG. 5 illustrates an example of prompts displayed on a control monitor 152 or suite monitor 126 of the system 100.

FIG. 5 illustrates an example of probe prompts displayed on the monitor 152. In an example, the ablation application 228 displays a set of default arrangements of probes. The arrangements may appear as a predefined geometric arrangement based on the number of probes to be selected for the ablation procedure (e.g., 3 probes—triangle, 4 probes—square or trapezoidal, 5 probes—circular, and so on). In FIG. 5, the monitor 152 presents the user with a prompt 510 to select a number of desired probes and a prompt 512 to select a type of probe. The user may be presented with icons representative of probe arrangements 501 (one probe), 502 (two probes), 503 (3 probes), 504 (4 probes), 505 (5 probes) and 506 (other number of probes). Upon selecting any of the icons 501 to 506, the planning software presents the user with additional icons 514-518 representative of probe types (sphere-type probe 514, rod-type probe 516, seed-type probe 516, and the like). To ensure, the user has made the proper selection, the planning software further presents the user with an additional select icon 520 to confirm selection. In an example, the control room user 14 selects 3-probes in a triangle pattern by using the mouse 156 to click on the 3-probes icon 503.

According to the number of probes and the shown geometrical formation (e.g., triangle for 3 probes) selected by the user, the planning software sets a maximum distance between probe tips. For example, a two centimeters probe tip to probe tip distance would work to ensure the formation of a synergistic ice ball having a radius of at least two centimeters (assuming an overlap of one centimeter). More than two centimeters distance between the tips of the probe increases a probability of forming a non-synergistic ice ball such that the ablation procedure would not be successful. In other embodiments, other maximum distances could be manually set by the clinician, from a look-up table, from a combination of probe or energy source parameters, etc. Also, the maximum distance could be defined manually by relating to the size of the tumor so that the user can avoid unreasonable tip positioning with the given size of the tumor. Moreover, in the other embodiments, minimal distances could be manually set by the clinician. Notably, a minimal distance between probe tips would be useful to avoid possible collision of the probes with each other.

Referring back to FIG. 4, at step 412, the method 400 enters a refining/editing step. Here, the ablation application 228 receives inputs and provides visual feedback on monitor 152 regarding refining/editing an arrangement and trajectory if needed for all of the probes 116. This occurs until the ablation application 228 receives input that the clinician 10 is satisfied with the proposed ablation zone. In this step, the refinement may be, for example, a refinement of a single probe position or may be an adjustment of the entire probe arrangement.

At step 414, the ablation application 228 prompts the clinician 10 to select a type of ablation probe and to choose ablation settings. Here, the probe prompt 512 in FIG. 5 also displays various icons 514, 516, 518 corresponding to probe types according to a shape of the output of each probe. In an example, the control room user 14 selects a sphere probe by using the mouse 156 to click on the sphere-type icon 514. At step 416, the ablation application 228 receives the selection in response to the control room user 14 pressing the select button 520.

At this point, the ablation application 228 includes information specifying an ablation zone center, one skin entry point, a trajectory between the two, a quantity of probes in a predefined arrangement (e.g., 3-probes in a triangle pattern), a type of ablation probe, and ablation settings. At step 418, the ablation application 228 utilizes this core information to generate a proposed ablation zone to enclose the targeted biological object.

The generation of the proposed ablation zone at step 418 involves a variety of determination. For example, based on the core information, the skin entry point of each of the three probes 116 are determined and the proposed location of the physical tip of each of the three probes in the tumor is determined. Since the tip of the probe here represents the core of ablation zone of each probe 116 and the core of ablation zone of each probe 116 would be slightly different that the physical tip of the probe, the ablation application 228 would calculate the physical tip of the probe 116 after the type of probe is specified at step 414 and optionally display a message on the suite monitor 126 to let the clinician 10 know about the exact depth at where the probe needs to be inserted. Calculating the physical tip of the probe 116 may include determining third points corresponding to tips of the probes 116 of the number in the image, based on the determined first point and the obtained geometry information.

Figure 11A:
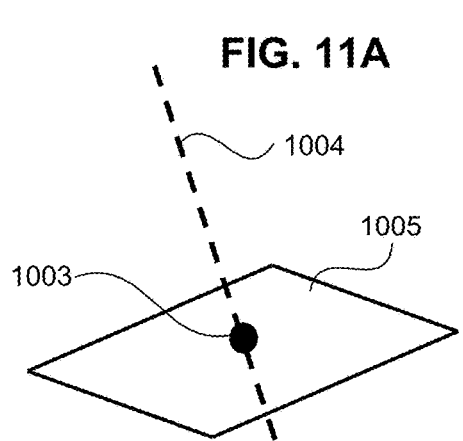
FIGS. 11A, 11B, and 11C illustrate exemplary processes carried out at steps 412 through 418.
Figure 11B:
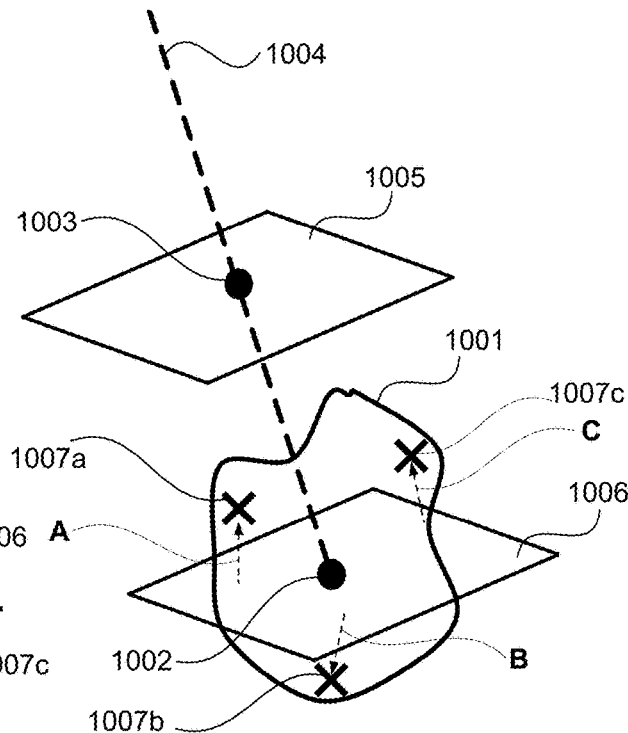
Figure 11C:
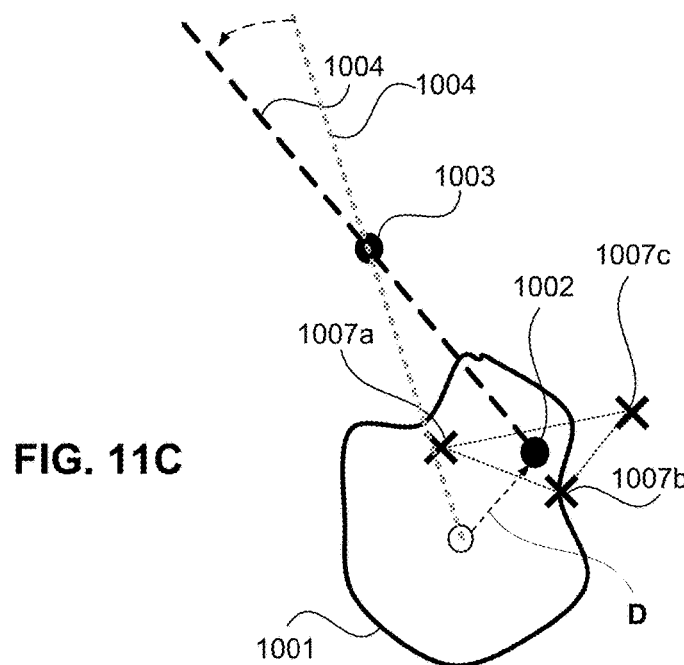

FIGS. 11A, 11B, and 11C illustrate exemplary processes carried out at steps 412 through 418 for refining and editing the arrangement of one or more of a first point 1002, second point 1003, and third points 1007a, 1007b, and 1007c. To modify one or more of the third points 1007a, 1007b, and 1007c from the initial position shown in FIG. 10B, the user can move the third point 1007a, 1007b, or 1007c on the working plane 1006, for example, by changing the distance between any of two or more points, as shown in FIG. 11A. During this manipulation, the user can confirm the two-dimensional view of the working plane with the contour of the tumor region 1001 and the first point 1002. Also, the user can move one or more of the third points 1007a, 1007b, and 1007c in a direction away from (above or below) the working plane 1006, as shown in FIG. 11B. In FIG. 11B, the user has moved the third point Iowa perpendicularly with respect to the working plane 1006 by distance A. Similarly, the user has moved the third point 1007b by a distance B away (below) the working plane 1006. And the user has moved the third point 1007c be a distance C above the working plane 1006 in a direction substantially parallel to reference trajectory 1004. With the manipulation exemplified by FIGS. 11A and 11B, the user can adjust the positions one or more of the third points 1007a, 1007b, 1007c freely in three-dimensional space while the user can visually assess the geometrical relationship of each of the third points with the working plane 1006, with the first point 1002, with the reference trajectory 1004 and the contour of the tumor region 1001.

As illustrated in FIG. 11C, the user can also move the first point 1002 in the three-dimensional space. When the first point 1002 is moved by a distance D, the planning software causes the CPU 202 to also move the third points 1007a, 1007b, 1007c together with the first point 1002 while maintaining fixed the relative positions and distances between the first point 102 and third points 1007a, 1007b, and 1007c. At the same time, the planning software updates the reference trajectory 1004 by connecting the first point 1002 and the second point 1003. In other words, in response to the user moving the first point 1002 in any direction within the three-dimensional space, the planning software of ablation application 228 causes the CPU 202 to immediately update reference trajectory 1004 and also move the third points 1007-1007c, while maintaining the arrangement of the third points 1007a, 1007b, 1007c with respect to the first point 1002 and the reference trajectory 1004. In this manner, the movement of one point along the reference trajectory 1004 produces a synergistic effect of repositioning all of the third points 1007a-1007c which represents a synergistic repositioning of the tips of the plurality of probes 116. In the same manner, the user can move the second point 1003 in the three-dimensional space. When the second point 1003 is moved (e.g., the insertion location is changed), the planning software updates the reference trajectory 1004 by connecting the first and the second point 1002 and 1003. However, in the case where the second point 1003 is moved within the reference plane 1005 (e.g., when the insertion location is changed, but the distance between reference plane 1005 and working plane 1006 does not change), the planning software does not update the position of (does not move) the thirds points 1007a, 1007b, 1007c.

After defining the positions of the first point 1002, the second point 1003, and the third points 1007a, 1007b, 1007c, the planning software generates an insertion trajectory plan for each probe based on the geometrical relationship between the reference trajectory 1004 and the edited position of the first, second and third points 1002, 1003, 1007a, 1007b, 1007c. Here, the insertion trajectory plan for each probe can be generated in various ways.

Figure 12A:
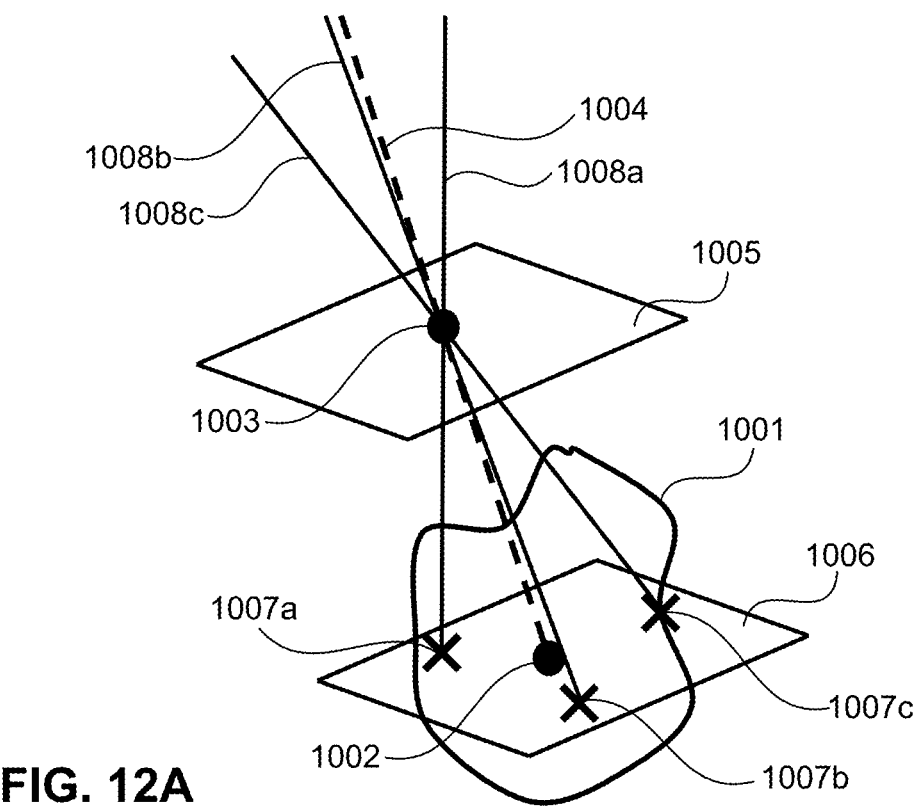
FIGS. 12A and 12B show examples of insertion trajectories generated by the system 100.
Figure 12B:
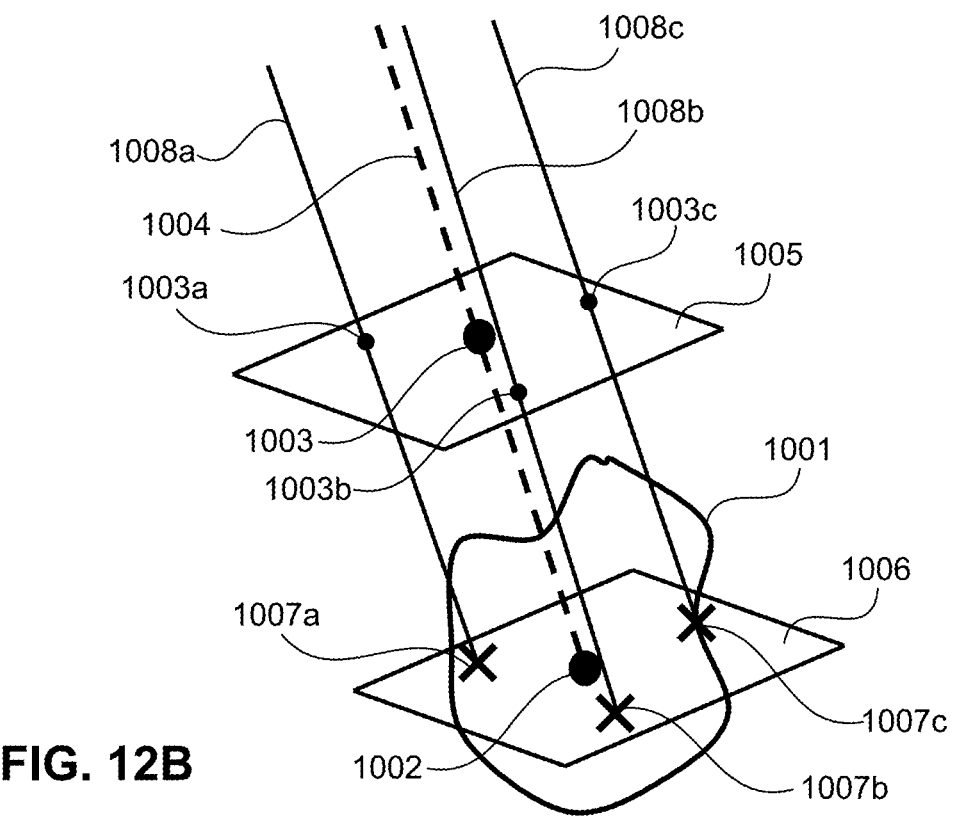

FIGS. 12A and 12B show examples of insertion trajectories for each of three probes generated by the planning software of ablation application 228. FIG. 12A shows a first embodiment of how to generate the insertion trajectory plan by using the reference trajectory 1004 defined by the first and the second points 1002 and 1003, and the corresponding reference and working planes 1005 and 1006. In this example shown in FIG. 2A, the planning software generates insertion trajectories 1008a, 1008b, and 1008c by connecting the second point 1003 to each of the third points 1007a, 1007b, 1007c. Since the reference trajectory 1004 is defined by the line including the first point 1002 (center of tumor) and the second point 1003 (skin entry point), the reference trajectory 1004 and insertion trajectories 1008a-1008c share the second pint 1003 as a common point to form a triangular pyramid. Advantageously, in this case, the user can use the reference trajectory 1004 to confirm the relative relationship between the probe insertion trajectories 1008a, 1008b, 1008c against the reference trajectory 1004 and the tumor region 1001. The configuration of planning probe-insertion trajectories by sharing a single skin entry point (second point 1003), as shown in FIG. 12A, would be particularly advantageous in minimizing discomfort to the patient, in maintaining the position of the needle/probe guide 112 fixed during needle insertion, which would be useful for cryoablation as well as microwave ablation.

FIG. 12B shows a second embodiment of how to generate the insertion trajectory plan by using the reference trajectory 1004 defined by the first and the second points 1002 and 1003. In the example shown in FIG. 12B, the planning software generates a plurality of insertion trajectories 1008a, 1008b, 1008c in parallel to the reference trajectory 1004, by generating a plurality of lines (vectors) originating at each the third points 1007a, 1007b, 1007c and extending in the same orientation and direction as (parallel to) that of reference trajectory 1004. In the example shown in FIG. 12B, the second point 1003 will not be used as the skin entry point. Instead, the planning software of ablation application 228 uses the second pint 1003 as a centroid for the insertion points, and uses the reference plane 1005 to generate a plurality of skin entry points 1003a, 1003b, 1003c, which are given by the intersection of the insertion trajectories 1008a, 1008b, 1008c with the reference plane 1005. As it will be recalled from FIG. 10A, the reference plane 1005 is defined substantially at the patient's skin surface. Therefore, in the case illustrated in FIG. 12B, the planning software can automatically define not only a plurality of planned insertion trajectories 1008a, 1008b, 1008c, but also the plurality of planned skin entry points 1003a, 1003b, 1003c. This configuration of defining a plurality of insertion trajectories 1008a-1008c parallel to the reference trajectory 1004 defined the first and the second points 1002 and 1003, would be particularly useful for irreversible electroporation where separate probes can be independently guided. In any of the above embodiments, the reference plane 1005 can be defined as expecting to be the mounting plane for the probe guide 112 (patient mount unit) for probe guidance on the patient skin surface. The planning illustrated in FIGS. 12A and 12B can be applicable regardless of whether the multiple probes are to be inserted simultaneously or sequentially. However, since the use of multiple probes can involve using probes having different structure (e.g., different tip size or shape) to cover irregularly shaped tumors, in some embodiments, the planning may be more advantageous in the case where the probes are inserted simultaneously because the planning software can visualize and adjust the probe trajectories taking into consideration any possible obstacles. This is in contrast to current practice where confirmation and/or adjustments are needed between each probe placement.

Figure 13:
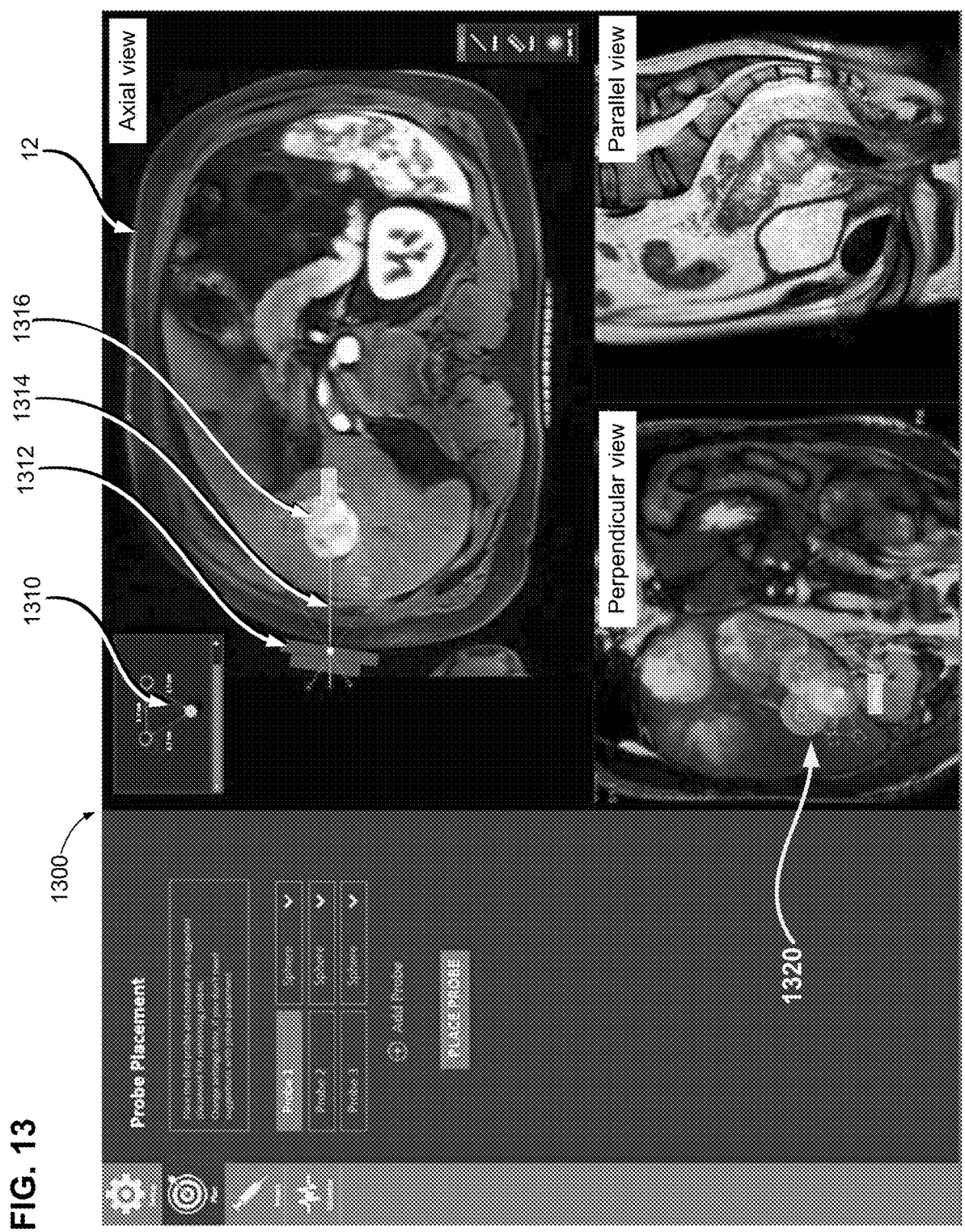
FIG. 13 illustrates an example of the graphical user interface (GUI) 1300 for the system 100.

Referring back to FIG. 4, at step 420, the ablation application 228 causes the suite monitor 126 and the control room monitor 152 to display the proposed ablation zone base on the ablation setting chosen in step 414. Here, the ablation application 228 may cause the control monitor 152, the suite monitor 126, or both of these monitors to display at least a part of the image and line segments representing the insertion trajectories of the probes 116, passing through the determined second point and the determined third points. In an example, the ablation application 228 displays a graphical user interface (GUI) having multiple pictures each corresponding to a number of probes, and each illustrating information corresponding to a number of probes. FIG. 13 illustrates an example of the graphical user interface (GUI).

At step 422, the ablation application 228 determines whether it has received an input indicating that the clinician 10 is satisfied with the proposed ablation zone. If the input at step 422 indicates that the clinician 10 is satisfied with the proposed ablation zone (YES at step 422), the method proceeds to a step 424. If the input at step 422 indicates that the clinician 10 is not satisfied with the proposed ablation zone (NO at step 422), the method 400 returns to step 412.

Assume that the clinician 10 is not satisfied at step 422 with the proposed ablation zone (NO at step 422) and the method 400 has returned to step 412. Recall that the method 400 enters a refining/editing step at step 412. Here, the clinician 10 can direct the control room user 14 to edit the default probe arrangement. The arrangement of the probes 116 may appear on the control monitor 152 along the defined trajectory as a group. In this regard, the ablation application 228 is configured to control all three probes in the arrangement to be edited together without selecting and editing them individually. For example, the control room user 14 can use to the ablation application 228 to move the arrangement of the probes together as a group by selecting and dragging the reference trajectory 1004 to a desired location. The control room user 14 can use to ablation application 228 to rotate the arrangement of probes around the reference trajectory 1004 by selecting one of the third points 1007a, 1007b, 1007c or one of the insertion trajectories 1008a, 1008b, 1008c, and using rotation arrows if the GUI. In an example, in response to a user input, the ablation application 228 performs control to move displayed third points 1007a-1007c corresponding to the tips of the probes 116.

Although the arrangement of the probes 116 may appear on the control monitor 152 along the defined trajectory as a group, the ablation application 228 may be also configured such that the control room user 14 can make a finer adjustment to each probe position by selecting and dragging a tip of a probe 116 individually; this can be carried out by moving independently one of the third points 1007a, 1007b, or 1007c, as shown in FIG. 11B. Dragging a tip of a probe 116 individually would result in the ablation application 228 changing the shape, size, area, or volume of the ablation zone. In an example, the ablation application 228 is configured to allow the control room user 14 to move a tip of a probe 116 closer to other probe tips, but prevent movement of a tip of a probe 116 beyond a predetermined maximum distance from the other probe tips. A reason for preventing movement of a probe tip beyond a maximum distance is that more than a predetermined maximum distance (e.g., two cm) between the tips of the probe increases the probability of formation of non-synergistic ice ball or thermal region to a point where the ablation procedure would not be sufficiently successful. For some embodiments, the ablation application 228 would provide control to issue a warning to the control room user 14 in case where a probe tip is moved more than the predetermined maximum distance from another probe tip. In issuing the warning (e.g., a visual or audible warning), ablation application 228 can issue a prompt to the user to verify if the probe should be moved more than the predetermined maximum distance. In an example, when the plurality of third points includes three or more points, in response to a user input to one of the third points, the ablation application 228 performs control to move a part of the third points based on a predetermined restriction of distances between at least two of the third points.

The ablation application 228 also is configured such that the control room user 14 can make a finer adjustment to the skin entry point by selecting and dragging the virtual skin entry point (second point 1003 in FIGS. 11A-11C) along the virtual grid on the scan slices. Moreover, the control room user 14 may be able to make adjustments to the reference trajectory 1004 by dragging the trajectory line with either the skin entry point or the center of ablation zone.

Assume that the clinician 10 is satisfied at step 422 with the proposed ablation zone (YES at step 422). Here, the method proceeds to step 424. At step 424, the ablation application 228 determines whether a request to create another ablation plan has been received. Allowing the clinician 10 to create two or more ablation plans will allow the clinician 10 to compare different options of probe placement to choose the most appropriate for the case. If the input received by the ablation application 228 at step 424 is a request to create another ablation plan (YES at step 424), the method 400 returns to step 402. If the input received by the ablation application 228 at step 424 is a request to not create another ablation plan (NO at step 424), the method 400 proceeds to step 308 in FIG. 3. Step 308 includes placing the probe guide 112 on the patient 12 and is discussed in detail in connection with a method 600 of FIG. 6.

FIG. 6 is a method 600 to place the probe guide 112 on the patient 12 to begin implementing an ablation plan developed in the method 400. As step 602, the ablation application 228 receives an input regarding a selected ablation plan for navigation. As step 602, the ablation application 228 causes the suite monitor 126 to display the position of the skin entry point with respect to, for example, the disposable skin marking grid on the sterile field. In one example, the clinician 10 physically marks the skin entry point on the patient 12 accordingly and removes the disposable skin marking grid. The clinician 10 sterilizes the area around the skin entry point. The probe guide 112 includes a probe guide sticker (or any appropriate marker) showing the center of the probe guide 112, so that the clinician 10 can position the probe guide 112 on the patient 12 by aligning the center of the probe guide 112 with the mark representing the skin entry point. The clinician 10 then removes the probe guide sticker and places the probe guide 112 on the skin of the patient.

After the clinician 10 positions the probe guide 112 on the patient 12, the clinician 10 may landmark the probe guide 112 to ensure that the probe guide 112 is well within the scan field of view. Here, the clinician 10 uses, for example, laser light from the scanner 140 to landmark the probe guide 112. At step 604, the ablation application 228 receives an input to realign the scan field of view (SFPV) to the center of the probe guide 112. The method 600 then proceeds to step 310 of FIG. 3. Step 310 includes registration of fiducials and is discussed in detail in connection with a method 700 of FIG. 7.

Figure 7:
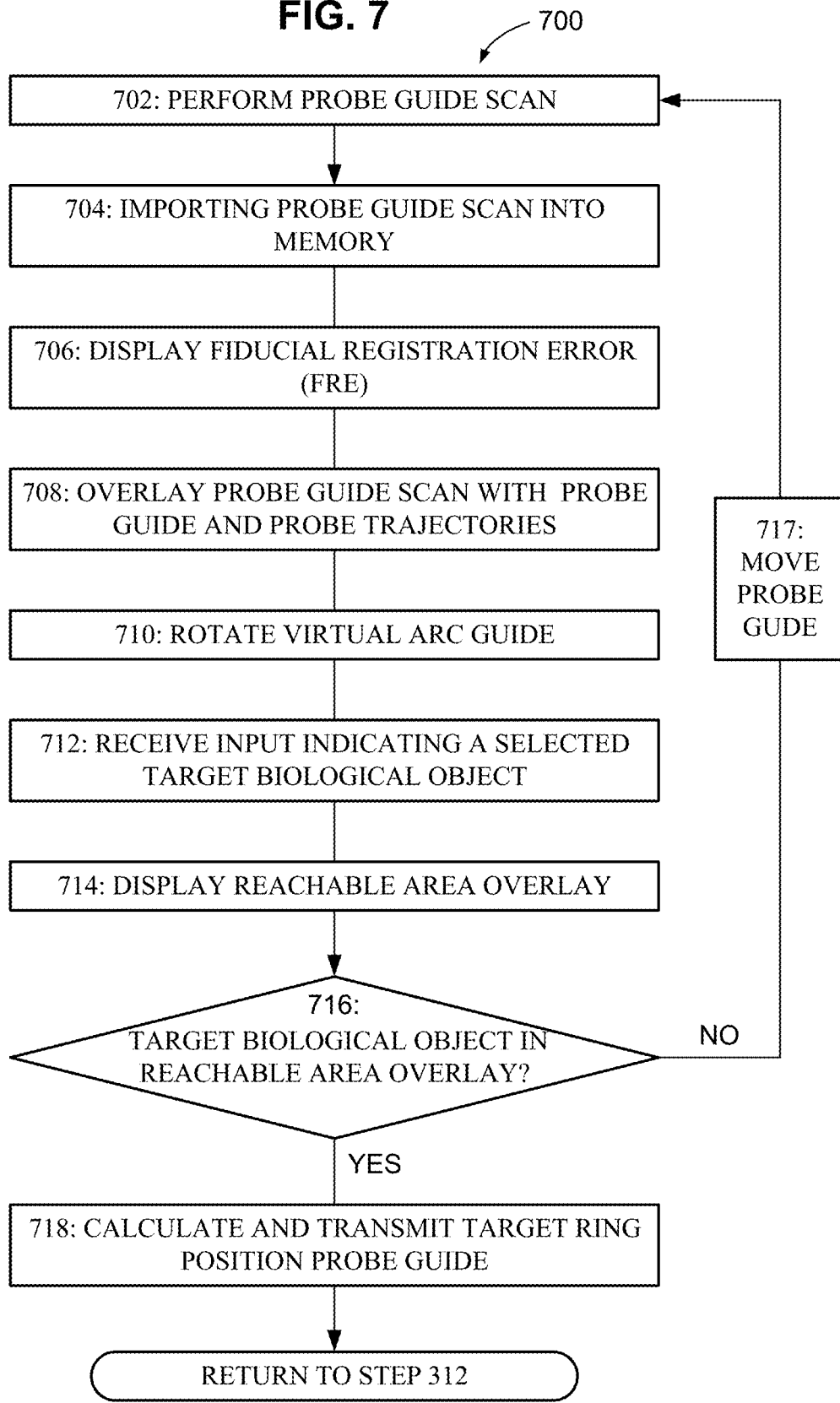
FIG. 7 is a method 700 showing a registration process to spatially register the plan developed in the method 400 with a probe guide 112 arranged on a patient 12.

FIG. 7 is a method 700 to register the position of the probe guide 112 on the patient 12, based on fiducial registration with the ablation application 228. A fiducial or fiducial markers are objects placed in the field of view of the scanner 140 so that the objects appear as a point of reference in an image produced by the scanner 140. At step 702, the ablation application 228 performs control to cause the scanner 140 to conduct a probe guide scan of the probe guide 112 on the patient 12. At step 704, the ablation application 228 imports the probe guide scan into the storage memory SSD 208 of ablation server 200. At step 706, the ablation application 228 automatically obtains information about fiducial locations and registers the probe guide to the patient image. Additionally, the ablation application 228 may calculate a fiducial registration error (FRE), and display the FRE on the suite monitor 126 and/or the control monitor 152. The clinician 10 may accept the registration of the probe guide 112 via a GUI of the suite monitor 126, the method 700 proceeds to step 708.

At step 708, the ablation application 228 causes the suite monitor 126 to overlay a virtual model of the probe guide 112 and planned probe trajectories on the displayed probe guide scan. The probe guide 112 comes with an arc guide and the displayed virtual probe guide 112 includes a virtual arc guide. At step 710, the ablation application 228 receives user input that causes the virtual arc guide of the probe guide 112 to rotate to define a guide device image-plane. At step 712, the ablation application 228 receives input indicating a selected target. The entry point and the positon of the targeted biological object may be different at this point due to organ motion or error in placement of the probe guide 112. In an alternative to step 710 and step 712, the ablation application 228 may receive adjustments to the planned trajectory based on, for example, real or calculated organ motion while the skin entry point is maintained the same as the center of the registered probe guide 112.

At step 714, the ablation application 228 causes a reachable area overlay to be displayed on the suite monitor 126. At step 716, the ablation application 228 determines whether it has received input indicating that the target biological object is within the reachable area overlay. If the target biological object is not within the reachable area overlay (NO at step 716), at step S717, the clinician 10 is directed to reposition (move) the probe guide 112 to the intended skin entry point and the method 700 returns to step 702. If the target biological object is within the reachable area overlay (YES at step 716), the method 700 proceeds to step 718 where the ablation application 228 calculates a target ring position and transmits the calculated target ring position and area to the probe guide 112. From the step 718, the method 700 proceeds to step 312 of FIG. 3. Step 312 includes navigating a ring of the probe guide 112 to a target position and partially inserting the probe 116 into the patient 12 and is discussed in detail in connection with a method 800 of FIG. 8.

FIG. 13 illustrates an example of the graphical user interface (GUI) 1300 to be displayed in control monitor 152 and/or suite monitor 126. As shown in FIG. 13, the GUI may display the scan slice (image) of the patient 12 (subject of needle/probe placement) in various views (e.g., an axial view, a parallel view, and a perpendicular view). The GUI 1300 shows a probe guide 1312 disposed (arranged) on the surface (skin) of the patient 12. To assist the user to intuitively plan the insertion trajectories for the probes, the planning software causes the GUI to display a reference trajectory 1314 defined by the center of a volume of interest 1316 and a skin entry point located on a plane where the probe guide 1312 is arranged. In addition, to allow the user to visualize the arrangement of the probe tips, the GUI displays a geometric arrangement 1320 of the probe tips corresponding to a predefined probe arrangement 1310 which has been selected by the user via prompts 510 and 512 (of FIG. 5).

Viewing the target area or tumor in the context of the probe guide 1312 is advantageous as the probe guide is going to act as a reference point (point of insertion) for the physicians. Then, the perpendicular view is set up as a plane from physician's point of view showing "down the barrel" from the probe guide 1312. The parallel view is set up perpendicular to the "down the barrel" view to let the physician examine the tumor and iceball from all sides.

Figure 14:
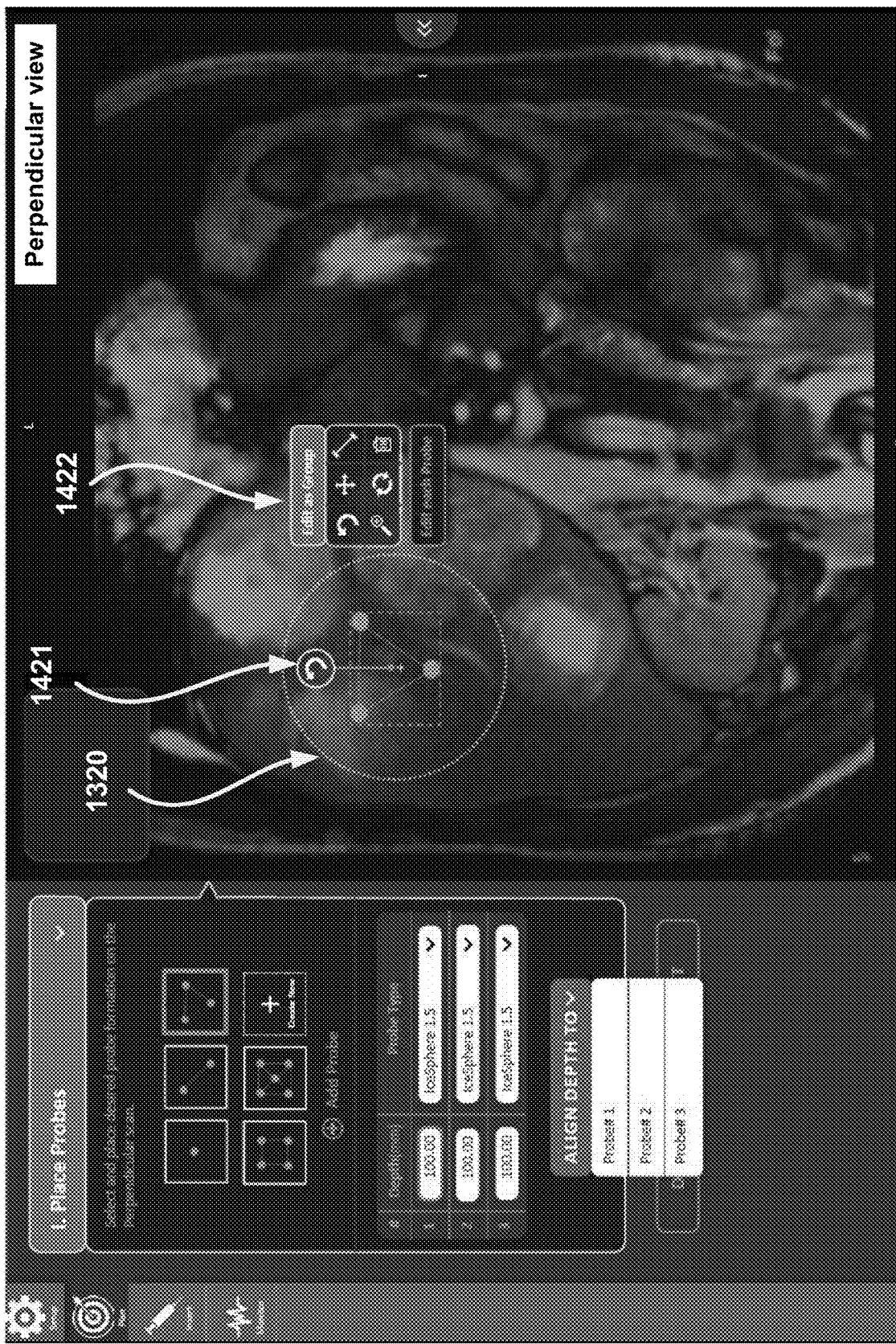
FIG. 14 illustrates an exemplary perpendicular view which can be displayed by the planning software in the control monitor 152 during the planning phase.

FIG. 14 illustrates an exemplary perpendicular view which can be displayed by the planning software in the control monitor 152 during the planning phase. As shown in FIG. 14, the GUI provides an interactive editing menu 1422 which allows the user to edit the position of the probes tips "as Group" or to edit "each probe". The geometric arrangement 1320 and/or position of the probes can be edited by intuitive group editing menus 1421. The perpendicular view allows the user to observe the geometric arrangement of the probes and the distance between the probe tips within the region of interest (tumor). The distance between the tips of the probe is important for maintaining synergy of the resultant iceball. For that reason, the distance between the tips of the probes should not exceed a predetermined maximum distance (e.g., 22 mm or 2.2 cm). During the planning phase, the perpendicular view is used by the intervention radiologist to scroll through different scan slices and edit the probe positions while observing the tips of the probes and distance between them at all times to reassure the probe tips will form an appropriate iceball.

Figure 15:
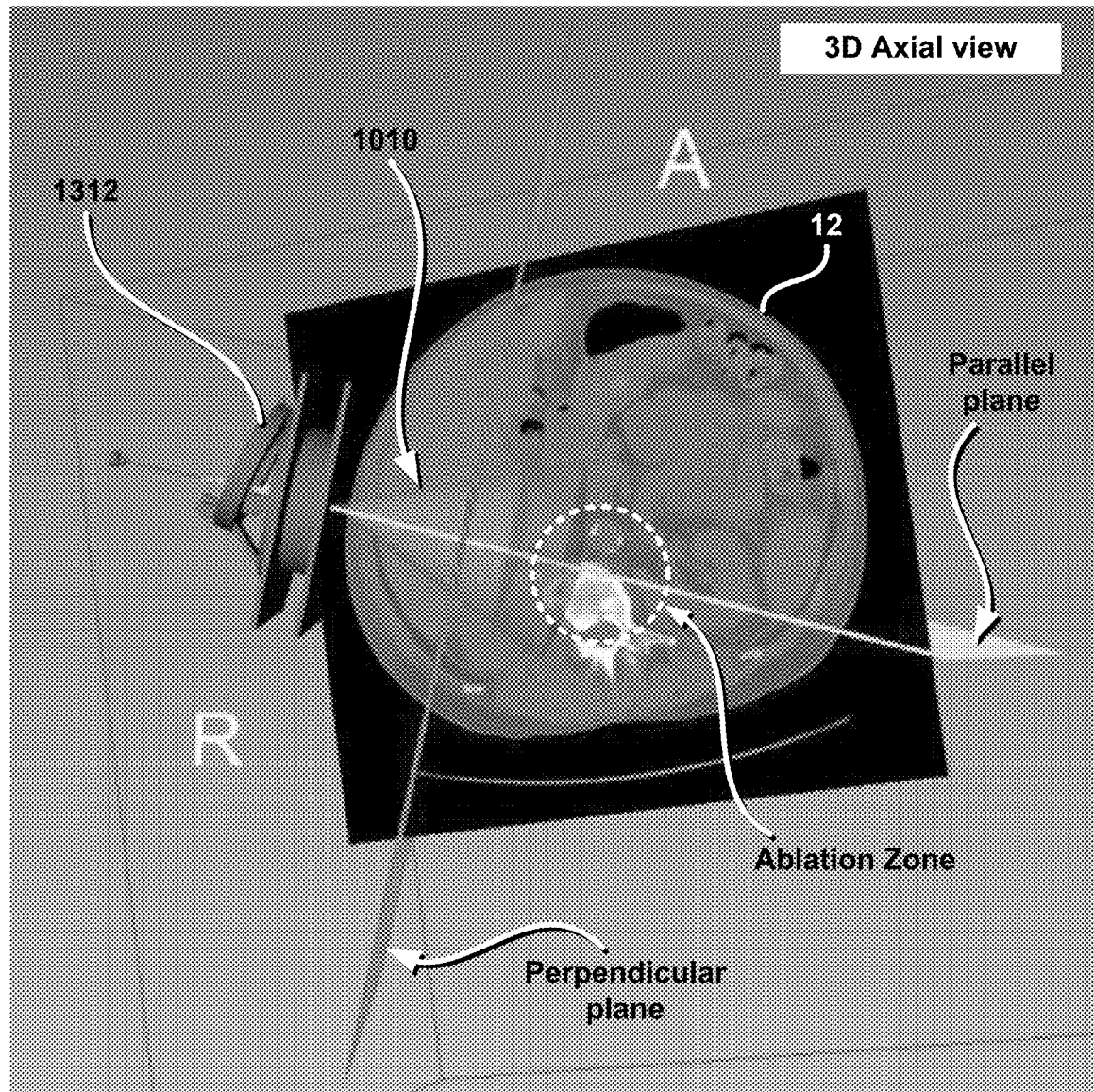
FIG. 15 illustrates an exemplary 3D axial view which can be displayed by in the control monitor 152.

The axial view is generally considered to be the most accurate view as all other views are reconstructed from the axial view unless the scan is specifically set at a desired plane. In the ablation application 228, the axial view can advantageously show the planned insertion trajectories and the area of coverage that can be covered by the probe guide 1312. FIG. 15 illustrates an exemplary 3D axial view which can be displayed by in the control monitor 152. In the axial view of FIG. 15, the display shows a 3D representation of the exemplary probe guide 1312 mounted on the surface (skin surface) of patient 12. From the axial view the user can observe the area of coverage 1010 (approachable area cone) that can be accessed with the probe guide 1312. The approachable area cone defines an area or volume inside the patient which is accessible to the probes by using the probe guide 1312. The potential ablation zone (tumor) should be well inside the area of coverage 1010 in order to insert the probe(s) using the probe guide. This cone can also be displayed in the other 2 views of the user interface to provide a reference to the user. Depending on how close the tip of a probe is from the edge of the cone, a warning could be displayed or emitted to prompt the user to edit the planned insertion trajectories of the probes, or to reposition the probe guide 1312. FIG. 8 is a method 800 of navigating a ring of the probe guide 112 to a target position. At step 802, the ablation application 228 receives information identifying a probe 116 selected to be inserted into the patient 12. At step 804, the probe guide 112 receives the calculated target ring position transmitted in step 718 by the ablation application 228 residing in the ablation server 200. At step 806, the ablation application 228 rotates a moveable ring on a base plate of the probe guide 112. Once the moveable ring reaches a predetermined ring position, the clinician 10 positions the arc guide on the probe guide 112. At this point, the clinician 10 partially inserts the selected ablation probe 116 using angle information on the arc guide. From the step 806, the method Boo proceeds to step 314 of FIG. 3. Step 314 includes updating the preliminary ablation plan created in step 306 to finalize the insertion of the probe 116 and is discussed in detail in connection with a method 900 of FIG. 9.

FIG. 9 is a method 900 for updating the preliminary ablation plan created in step 306 to finalize the insertion of the probe 116. At step 902, the ablation application 228 performs control to cause the scanner 140 to conduct a scan. The method 900 then performs steps similar to steps 702, 706, and 706 in method 700 of FIG. 7. At step 904, the ablation application 228 performs control to cause the scanner 140 to conduct a probe guide scan of the probe guide 112 on the patient 12. At step 906, the ablation application 228 imports the probe guide scan into the SSD 208. At step 908, the ablation application 228 automatically registers the fiducials, calculates a fiducial registration error (FRE), and displays the FRE on the suite monitor 126 and the control monitor 152. Once the clinician 10 accepts the registration of the fiducial markers via a GUI of the suite monitor 126, the method 900 proceeds to step 910.

At step 910, the ablation application 228 receives input identifying the tip of the probe 116 partially inserted into the patient 12 after step 806 of FIG. 8. At step 912, the ablation application 228 displays an image showing the actual trajectory traveled by the probe 116 into the patient 12 overlain with the proposed (planned) trajectory set out in the ablation plan created in step 306. At step 914, the ablation application 228 determines whether it has received information indicating that the probe 116 has been inserted along the desired (planned) trajectory. If the probe 116 has been inserted along the desired trajectory (YES at step 914), the method 900 proceeds to step 916. If the probe 116 has not been inserted along the desired trajectory (NO at step 914), the method 900 proceeds to step 915. At step 915, the user may be prompted to make a minor change to the probe trajectory or to edit the planned trajectory.

A change to the probe trajectory can be implemented by, for example, slightly rotating the movable ring on the base plate of the guide by a fraction of degree or a few degrees. However, in the case where the probe trajectory cannot be changed to match the planned insertion trajectory, the user may update the planned trajectory during the insertion operation. More specifically, if the ablation application 228 determines at step S914 that the probe is not being inserted along a pre-planned trajectory, it is possible that the probe has to be inserted along an unplanned trajectory to avoid damaging healthy tissue or to avoid touching delicate organs surrounding the tumor. In this case, the ablation application 228 can allow the user to make quick modifications to the planned trajectories, for example, by the user simply moving at least one of the third points 1007a, 1007b, 1007, or moving the first point 1002, as shown in FIGS. 11B and 11C. As noted above, to maintain synergistic effect, the ablation application 228 causes the planned trajectories to be moved (updated) as group if the first point 1102 is moved or even if only one of the third points 1007a, 1007b, 1007c is moved as shown in FIG. 11C.

Therefore, at step 915, the ablation application 228 receives changes to the desired trajectory to cause the tip of the probe 116 to be redirected to a newly planned trajectory and reach its intended target. After the changes, are made the ablation application updates the ablation plan and returns to step 912 to again display the actual probe trajectory over the planned trajectory. At step 914, the ablation application 228 determines whether the probe 116 has been inserted along the desired trajectory. If the probe 116 has been inserted along the desired trajectory (YES at step 914), the method proceeds to step 916. From step 916, the method 900 proceeds to step 918.

At step 918, the ablation application 228 determines whether the probe 116 has reached the predetermined depth. In an example, the predetermined depth is 100 millimeters (about four inches) for the patient's skin insertion point (second point 1003). If the probe 116 has not reached the predetermined depth (NO at step 918), the clinician 10 continues to insert the probe 116 into the patient 12 while the method 900 returns to step 914. The process of S912, S914, S915, S916, and S918 is iteratively repeated while the user continuously observes that the probe is being inserted along the desired trajectory and confirms that it has reached a predetermined depth (e.g. the depth of the tumor). If the probe 116 has reached the predetermined depth (YES at step 918), the method 900 proceeds to step 920.

At step 920, the ablation application 228 determines whether all the probes 116 selected in step 410 of FIG. 4 have been inserted. If the selected quantity of probes 116 have not been inserted (NO at step 920), the clinician 10 removes the arc guide from the probe guide 112 and the method 900 proceeds to step 312. If the selected quantity of probes 116 have been inserted (YES at step 920), the method 900 proceeds to step 318. Steps 318-324 were discussed above in reference to FIG. 3.

The system and method for planning multiple-probe ablation provides a variety of benefits. Using a computer-implemented system and method equipped with the ablation application 228, the clinician 10 can plan placement of multiple ablation probes by defining only one reference trajectory based on a line connecting a skin entry point and a center of a tumor or lesion. In this manner, the clinician 10 not need select a skin entry point and target point for every probe intended to use. As a result, the ablation application 228 requires fewer click inputs in assisting the clinician 10 in planning multiple probes during an ablation procedure.

Since planning the trajectories of multiple probes is carried out by placing the probes as a group along a reference trajectory, the trajectory of each probe does not need to be individually edited unless needed, for example, to avoid obstacles for each individual probe. Thus, the clinician 10 may take less variables into consideration while refining probe trajectory. This results in a more expeditious pre-planning process as compared to the planning of each probe trajectory individually. During an ablation procedure, the clinician 10 can focus on creating a synergistic ablation zone, rather than focusing on fine probe placement of each individual probe. The method and system controlled by the ablation application 228 allows users to think about multiple probes as a group with one synergistic ablation zone.

A clinician 10 may place probes equidistant to each other so that the resultant placement will have synergistic ablation zone (such as formation of a synergistic ice ball). Using the ablation server 200 having the ablation application 228 stored therein, the clinician 10 can create a synergistic ablation zone. By placing the chosen number of probes 116 in a predetermined geometric arrangement, the ablation application 228 enables the user to effortlessly create the synergistic ablation zone.

Sometimes, the clinician 10 may prefer to experiment with different number of probes 116 to see how many probes 116 are required to ablate a particular tumor. The clinician 10 may be able to do this using the ablation application 228 by selecting the number of probes and viewing the probe arrangement displayed by the ablation application 228. As explained with reference to the algorithm of FIG. 9, the ablation application 228 may operate to reduce the number of iterations for the determination of the insertion point(s) and trajectory of the probe after the probe is inserted into the entry point(s). This is beneficial for reducing exposure to radiation when dealing with CT scans and reduces the total time of scanning when dealing with any type of scan, including, but not limited to, CT, MRI, PET or otherwise.

The system and method for planning multiple-probe ablation as disclosed herewith are particularly advantaged by the combination of the planning application with the patient skin-surface mounting device as described herein for both planning and guiding one or more probes to the target site. The patient skin-surface mounting device may be manual, completely automated in delivering the probes according to the planned trajectory, or some combination thereof, preferably including points where the clinician 10 may verify that the probes are being inserted according to the planned trajectories and to check that the planned procedure is effective for the patient's needs. Exemplary patient skin-surface mounting devices are described, for example, in U.S. Pat. No. 9,222,996; U.S. Pat. Pubs. 2014/0275978, 2017/0000581, 2016/0074063, 2015/0238266, 2017/0071626, 2017/0014200, 2017/0030557, 2016/0074063, 2017/0172458 and 2018/0103979; PCT Publications WO2016/208711, WO2017/132505, and WO2017/180643; and U.S. patent application Ser. No. 15/808,703. The registration process described in U.S. Pat. Pub. 2017/0000581 may be complemented with, or used in executing the planned procedure described herein. Each of the references in this paragraph are hereby incorporated by reference in their entirety for all purposes.

Any methods and/or data of the present disclosure, such as the methods for performing ablation planning and/or performance, radiotherapy, or otherwise as discussed herein, may be stored on a computer-readable storage medium. A computer-readable and/or writable storage medium used commonly, such as, but not limited to, one or more of a hard disk, a flash memory, a CD, an optical disc (e.g., a compact disc (CD) a digital versatile disc (DVD), etc.), a magneto-optical disk, a random-access memory (RAM) (such as the RAM 204), a DRAM, a read only memory (ROM) (such as the ROM 206, a storage of distributed computing systems, a memory card, or the like (e.g., other semiconductor memory, such as, but not limited to, a non-volatile memory card, a solid state drive (SSD), SRAM, etc.), an optional combination thereof, a server/database, etc. may be used to cause a processor, such as, the processor or CPU 202 of the ablation server 200 to perform the steps of the methods disclosed herein.

Embodiment(s) also can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a non-transitory computer-readable storage medium) to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

LIST OF EXEMPLARY REFERENCES

The present disclosure provides significant useful improvements on conventional planning and navigation systems for ablation. Readers of the present disclosure may review the following lists of non-patent literature (NPL) and patent publications, which are considered "nonessential material", are hereby incorporated by reference herein in their entirety:

1. Liu S, Xia Z, Liu J, Xu J, Ren H, Lu T, et al., "Automatic Multiple-Needle Surgical Planning of Robotic-Assisted Microwave Coagulation in Large Liver Tumor Therapy", the public library of science (PLoS) ONE11(3):

e0149482. Published: Mar. 16, 2016, https://doi.org/10.1371/journal.pone.0149482;
2. MAXIO™ "Integrated planning, navigation and robotic targeting of tumor ablation", brochure published 2012;
3. Beyer et al., "Stereotactically-navigated percutaneous Irreversible Electroporation (IRE) compared to conventional IRE: a prospective trial", (2016), PeerJ, DOI 10.7717/peerj.2277;
3. Patent publications include: US 2014/0275978, US 2018/0103979, US 2017/0079720, US 20170100195, US 2016/0113662 and U.S. Pat. No. 9,144,461.

What is claimed is:

1. A method of performing planning for a percutaneous multi-probe treatment, comprising:
   acquiring a scan image of an object to be treated with multi-probe percutaneous insertions;
   determining a first point in a region of interest (ROI) in the scan image;
   determining one or more second points at a surface of the object in the scan image;
   generating a reference trajectory by connecting the first point with one second point;
   arranging, around the first point, a number of third points corresponding to tips of probes to be inserted into the object;
   generating line segments representing planned insertion trajectories for the probes based on the number of probes to be inserted and on the reference trajectory; and
   causing a monitor to display superposed on the scan image at least one of the planned insertion trajectories,
   wherein the planned insertion trajectories extend in a geometric relationship to the reference trajectory and pass through the third points and through one or more second points, and
   wherein the reference trajectory does not represent an insertion trajectory for a probe but serves as a geometric centroid for the planned insertion trajectories.

2. The method according to claim 1, further comprising:
   selecting the number of probes and a type of probe for each of the probes to be inserted into the object; and
   obtaining, based on the number of probes to be inserted into the object, a geometry of tips of the probes to be inserted.

3. The method according to claim 1, further comprising:
   generating a reference plane which is perpendicular to the reference trajectory and passes through the one or more second points; and
   generating a working plane which is parallel to the reference plane and passes through the first point.

4. The method according to claim 3,
   wherein the first point is at or adjacent to a center of the ROI, and
   wherein the arranging the third points includes arranging the third points on the working plane and substantially equidistant from the first point.

5. The method according to claim 1, further comprising: determining whether the third points are arranged within the ROI.

6. The method according to claim 5, further comprising:
   in response to determining that at least one of the third points is not arranged within the ROI, moving one or more of the third points with respect to the first point such that all of the third points are arranged within the ROI.

7. The method according to claim 4, further comprising:
   moving at least one of the third points with respect to the first point,
   wherein, in response to moving the at least one of the third points, the method further comprises moving the remaining third points such that the third points maintain a geometry corresponding to the tips of the probes to be inserted.

8. The method according to claim 4, further comprising:
   moving the first point; and
   in response to moving the first point, automatically moving all of the third points such that the third points remain arranged around the first point while maintaining a predetermined distance between at least two of the third points.

9. The method according to claim 1,
   wherein each of the planned insertion trajectories respectively passes through one of the third points and all of the planned insertion trajectories pass through only one second point, such that each planned insertion trajectory intersects the reference trajectory at an angle.

10. The method according to claim 1,
    wherein each of the planned insertion trajectories respectively passes through one of the third points and through one of the second points, such that each planned insertion trajectory extends parallel to the reference trajectory and passes through a separate second point.

11. The method according to claim 1,
    wherein the acquiring a scan image includes acquiring an ultrasound image, a computer tomography (CT) image, or a magnetic resonance (MR) image of the object to be treated.

12. The method according to claim 11,
    wherein the scan image is a slice scan of a pre-acquired three-dimensional (3D) image obtained by ultrasound, CT, or MR imaging.

13. The method according to claim 1,
    wherein, during an interventional procedure in which a first probe is inserted a predetermined distance into the object, the method further comprising:
    determining whether the first probe has been inserted along a planned insertion trajectory; and
    in response to determining that the first probe has not been inserted along a planned insertion trajectory, updating the plurality of insertion trajectories by moving the first point within the ROI or moving all of the third points together with respect to the first point.

14. The method according to claim 3,
    wherein determining the one or more second points includes selecting one or more probe entry points in the scan image, and
    wherein generating the working plane includes defining a patient skin-surface mounting plane for receiving a probe guiding device to be mounted during probe insertion.

15. An apparatus for performing a percutaneous multi-probe treatment, comprising:
    a processor; and
    a memory storing program code representing instructions to cause the processor to:
       acquire a scan image of an object to be treated with multi-probe percutaneous insertions;
       determine a first point in a region of interest (ROI) in the scan image;
       receive input from a user who selects one or more second points at a surface of the object in the scan image;

generate a reference trajectory by connecting the first point to one second point;
arrange, around the first point, a number of third points corresponding to tips of probes to be inserted into the object;
generate line segments representing planned insertion trajectories for the probes based on the number of probes to be inserted and on the reference trajectory; and
cause a monitor to display superposed on the scan image at least one of the planned insertion trajectories,
wherein the processor generates the planned insertion trajectories extending in a geometric relationship to the reference trajectory and passing through the third points and through one or more second points, and
wherein the reference trajectory does not represent an insertion trajectory for a probe but serves as a geometric centroid for the planned insertion trajectories.

16. The apparatus according to claim 15, wherein the processor is further configured to:
prompt the user to select the number of probes and a type of probe for each of the probes to be inserted into the object; and
the processor selects, based on the number of probes to be inserted into the object, a geometry of tips of the probes to be inserted.

17. The apparatus according to claim 15, wherein the processor is further configured to:
generate a reference plane which is perpendicular to the reference trajectory and passes through the one or more second points; and
generate a working plane which is parallel to the reference plane and passes through the first point.

18. The apparatus according to claim 17,
wherein the first point is at or adjacent to a center of the ROI, and
wherein the processor is further configured to arrange the third points on the working plane and substantially equidistant from the first point.

19. The apparatus according to claim 15, wherein the processor is further configured to determine whether the third points are arranged within the ROI.

20. The apparatus according to claim 19, wherein the processor is further configured to,
in response to determining that at least one of the third points is not arranged within the ROI, move one or more of the third points with respect to the first point such that all of the third points are arranged within the ROI.

21. The apparatus according to claim 15, wherein the processor is further configured to receive an input from the user selecting one second point as either a single entry point or a center position among plural entry points for the probes to be inserted.

22. The apparatus according to claim 19, wherein the processor is further configured to
move at least one of the third points with respect to the first point,
wherein, in response to moving the at least one of the third points, the processor further moves the remaining third points such that the third points maintain a geometry corresponding to tips of the probes to be inserted.

23. The apparatus according to claim 19, wherein the processor is further configured to
move the first point; and in response to moving the first point, the processor automatically moves all of the third points such that the third points remain arranged around the first point while maintaining a predetermined distance between at least two of the third points.

24. The apparatus according to claim 15,
wherein the processor generates the planned insertion trajectories such that one planned insertion trajectory passes through each of the third points and all planned insertion trajectories pass through only one second point, such that each planned insertion trajectory intersects the reference trajectory at an angle.

25. The apparatus according to claim 15,
wherein the processor generates the planned insertion trajectories such that each one the planned insertion trajectories pass through one of the third points and through one of the plurality of second points, such that each planned insertion trajectory extends parallel to the reference trajectory and passes through a separate second point.

26. The apparatus according to claim 15,
wherein the processor is further configured to acquire, as the scan image, an ultrasound image, a computer tomography (CT) image, or a magnetic resonance (MR) image of the object to be treated.

27. The apparatus according to claim 26,
wherein the processor is further configured to acquire, as the scan image, a slice scan of a previously acquired three-dimensional (3D) image obtained by ultrasound, CT, or MR imaging.

28. The apparatus according to claim 15,
wherein, during an interventional procedure in which a first probe is inserted a predetermined distance into the object, the processor is further configured to:
determine whether the first probe has been inserted in a geometric relationship to a planned insertion trajectory; and
in response to determining that the first probe has not been inserted in a geometric relationship to a planned insertion trajectory, the processor updates the plurality of insertion trajectories by moving the first point within the ROI or moving all of the third points together with respect to the first point.

29. The apparatus according to claim 17, wherein the processor is further configured to prompt the user to selects the one or more second points, one or more probe entry points in the scan image, and
wherein the processor generates the working plane as a patient skin-surface mounting plane for receiving a probe guiding device to be mounted during probe insertion.

30. The apparatus according to claim 15, further comprising:
a probe guide device configured to position each of the probes to be inserted into the object in a geometric relationship with respect to the reference trajectory, such that each probe to be inserted advances along one of the planned insertion trajectories,
wherein the processor is further configured to
control insertion of each of the probes along a corresponding planned insertion trajectory; and
cause the monitor to display at least one inserted probe trajectory superposed over a planned insertion trajectory.

31. A method for planning probe insertion in a multiple probe ablation procedure executed by an ablation server, the method comprising:

determining a first point in a tumor region in an image of an object to be examined;

determining a second point corresponding to multiple probe insertion at a surface of the object in the image;

defining a reference trajectory by connecting the first point with the second point;

obtaining number information regarding a number of probes to be inserted into the object;

obtaining geometry information of an arrangement of tips of the probes to be inserted, the geometry being associated with the obtained number information;

determining, based on the determined first point and the obtained geometry information, third points corresponding to the arrangement of tips of the probes to be inserted;

generating line segments representing insertion trajectories of the number of probes, wherein the insertion trajectories extend along the reference trajectory in a geometric relationship thereto, pass through the determined third points and intersect the surface of the object at or around the second point, and wherein the reference trajectory does not represent an insertion trajectory for a probe but serves as a geometric centroid for the insertion trajectories; and causing a monitor to display at least a part of the image and the line segments.

32. An ablation server storing an ablation application having instructions that, when executed by a processor, cause the ablation server to perform the method according to claim 31.

33. A non-transitory computer-readable storage medium storing an ablation application to cause an ablation server to perform the method according to claim 31.

* * * * *